US010772983B2

United States Patent
Fujita et al.

(10) Patent No.: US 10,772,983 B2
(45) Date of Patent: Sep. 15, 2020

(54) PERFUME RETAINER MEMBER AND AROMA PROVISION DEVICE

(71) Applicant: Sony Corporation, Tokyo (JP)

(72) Inventors: Shuji Fujita, Tokyo (JP); Tsunetoshi Samukawa, Kanagawa (JP); Koya Nomoto, Aichi (JP); Yuji Ishigaki, Tokyo (JP); Hideki Nakano, Aichi (JP); Keita Tanaka, Aichi (JP); Naoyuki Suzuki, Aichi (JP)

(73) Assignee: Sony Corporation, Tokyo (JP)

( * ) Notice: Subject to any disclaimer, the term of this patent is extended or adjusted under 35 U.S.C. 154(b) by 246 days.

(21) Appl. No.: 15/754,013

(22) PCT Filed: Mar. 31, 2017

(86) PCT No.: PCT/JP2017/013676
§ 371 (c)(1),
(2) Date: Feb. 21, 2018

(87) PCT Pub. No.: WO2018/003218
PCT Pub. Date: Jan. 4, 2018

(65) Prior Publication Data
US 2018/0243460 A1      Aug. 30, 2018

(30) Foreign Application Priority Data

Jun. 30, 2016  (JP) ................. 2016-130696

(51) Int. Cl.
*A61L 9/12*      (2006.01)
(52) U.S. Cl.
CPC .............. *A61L 9/12* (2013.01); *A61L 9/122* (2013.01); *A61L 2209/12* (2013.01); *A61L 2209/133* (2013.01)

(58) Field of Classification Search
CPC ........ A61L 9/12; A61L 9/122; A61L 2209/12; A61L 2209/133
(Continued)

(56) References Cited

U.S. PATENT DOCUMENTS 3,006,042 A * 10/1961 Calandra ............ B60H 1/00264
                                                              422/174
5,023,020 A *  6/1991 Machida ................. A61L 9/122
                                                              239/305

(Continued)

FOREIGN PATENT DOCUMENTS

CN       205093591 U    3/2016
EP        2347922 A2    7/2011
(Continued)

OTHER PUBLICATIONS

International Search Report and English translation thereof dated Jun. 13, 2017 in connection with International Application No. PCT/JP2017/013676.
(Continued)

*Primary Examiner* — Charles S Bushey
(74) *Attorney, Agent, or Firm* — Wolf, Greenfield & Sacks, P.C.

(57) ABSTRACT

A perfume retainer includes a main body and an air flow channel located in the main body. The air flow channel includes: a retainer space configured to retain a perfume, a first opening located connecting a first end of the retainer space to a space outside of a first end of the air flow channel, and a second opening connecting a second end of the retainer space to a space outside of a second end of the air flow channel. The retainer space includes a plurality of segment regions arranged adjacent each other such that an external wall of one of the plurality of segment regions is in contact with an external wall of another of the plurality of segment regions. The plurality of segment regions increase
(Continued)

a surface area of the air flow channel without increasing a volume of space of the air flow channel.

16 Claims, 35 Drawing Sheets

(58) Field of Classification Search
USPC .............................. 261/30, DIG. 88, DIG. 89
See application file for complete search history.

(56) References Cited

U.S. PATENT DOCUMENTS

| | | | | |
|---|---|---|---|---|
| 5,167,877 | A * | 12/1992 | Pai | A61L 9/122 261/18.1 |
| 5,565,148 | A * | 10/1996 | Pendergrass, Jr. | A61L 9/122 261/30 |
| 5,963,302 | A * | 10/1999 | Wittek | A61L 9/125 352/38 |
| 6,234,455 | B1 * | 5/2001 | Wittek | A61L 9/125 261/30 |
| 6,399,027 | B1 | 6/2002 | Shah et al. | |
| 6,713,024 | B1 * | 3/2004 | Arnell | A61L 9/125 239/57 |
| 7,045,000 | B2 * | 5/2006 | Kim | A61L 9/122 239/59 |
| 7,278,628 | B2 * | 10/2007 | Scholz | A61L 9/125 261/26 |
| 7,344,123 | B2 * | 3/2008 | Pankhurst | A61L 9/035 261/30 |
| 8,469,293 | B2 * | 6/2013 | Doty | A61L 9/122 239/44 |
| 2003/0020185 | A1 * | 1/2003 | Cox | A01M 1/2033 261/26 |
| 2003/0026728 | A1 * | 2/2003 | Avram | A63J 5/00 422/4 |
| 2011/0226866 | A1 | 9/2011 | Kim et al. | |

FOREIGN PATENT DOCUMENTS

| | | |
|---|---|---|
| JP | 3-114508 A | 5/1991 |
| JP | 05-082442 U | 11/1993 |
| JP | 2003-061545 A | 3/2003 |
| JP | 2005-082660 A | 3/2005 |
| JP | 2008-278770 A | 11/2008 |
| JP | 2014-067293 A | 4/2014 |
| WO | WO 2004/009142 A1 | 1/2004 |
| WO | WO 2010-044611 A2 | 4/2010 |

OTHER PUBLICATIONS

Extended European Search Report dated Mar. 19, 2020, in connection with European Application No. 17819587.1.

Chinese Office Action dated May 20, 2020, in connection with Chinese Application No. 201780002967.5, and English translation thereof.

* cited by examiner

B-B

PERFUME RETAINER MEMBER AND AROMA PROVISION DEVICE

CROSS-REFERENCE TO RELATED APPLICATIONS

This application is a U.S. National Stage entry under 35 U.S.C. § 371 of International Application No. PCT/JP2017/013676, filed in the Japan Patent Office on Mar. 31, 2017, which claims priority to Japanese Patent Application No. 2016-143635, filed in the Japan Patent Office on Jul. 21, 2016, and to Japanese Patent Application No. 2016-130696, filed in the Japan Patent Office on Jun. 30, 2016; each of these earlier applications is incorporated by reference herein in its entirety.

TECHNICAL FIELD

The present disclosure relates to a perfume retainer member and an aroma provision device.

BACKGROUND ART

In the related arts, technologies related to aroma provision devices configured to provide aroma have been proposed. For example, Patent Literature 1 proposes a technology of supplying air into a container device containing a perfume retainer body, outputting evaporated perfume by using an air flow, and providing aroma (see Patent Literature 1, for example).

CITATION LIST

Patent Literature

Patent Literature 1: JP 2014-67293A

DISCLOSURE OF INVENTION

Technical Problem

Meanwhile, when using the conventional technology, a large perfume retainer member may be necessary in the case where an amount of perfume is increased to improve aroma sustainability. In the case of making the perfume retainer member larger, an aroma provision device itself may also get larger. With regard to the aroma provision device, it is desirable to prevent the device from getting larger and improve the aroma sustainability more.

Accordingly, the present disclosure proposes a novel and improved perfume retainer member and aroma provision device that are capable of preventing the device from getting larger and improving aroma sustainability.

Solution to Problem

According to the present disclosure, there is provided a perfume retainer member including: a retainer space that is made in a main body to retain a perfume; and a first opening and a second opening configured to open the retainer space to an outside of the main body. An air flow channel includes the retainer space, the first opening, and the second opening.

In addition, according to the present disclosure, there is provided an aroma provision device including: a perfume retainer member including an air flow channel that includes a retainer space that is made in a main body to retain a perfume, and a first opening and a second opening configured to open the retainer space to an outside of the main body; and an air blow source configured to supply air to the air flow channel.

Advantageous Effects of Invention

As described above, according to the present disclosure, it is possible to prevent the device from getting larger and improve aroma sustainability.

Note that the effects described above are not necessarily limitative. With or in the place of the above effects, there may be achieved any one of the effects described in this specification or other effects that may be grasped from this specification.

MODE(S) FOR CARRYING OUT THE INVENTION

Hereinafter, (a) preferred embodiment(s) of the present disclosure will be described in detail with reference to the appended drawings. Note that, in this specification and the appended drawings, structural elements that have substantially the same function and structure are denoted with the same reference numbers, and repeated explanation of these structural elements is omitted.

Figure 1:
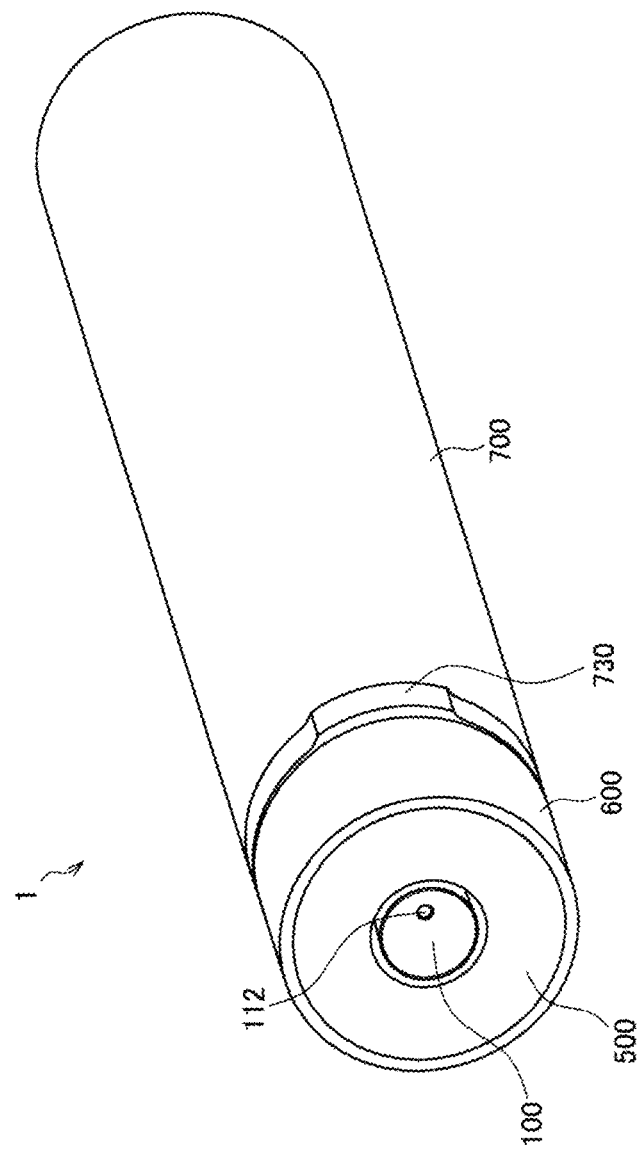
FIG. 1 is a perspective view illustrating an example of an aroma provision device according to an embodiment of the present disclosure.
Figure 2:
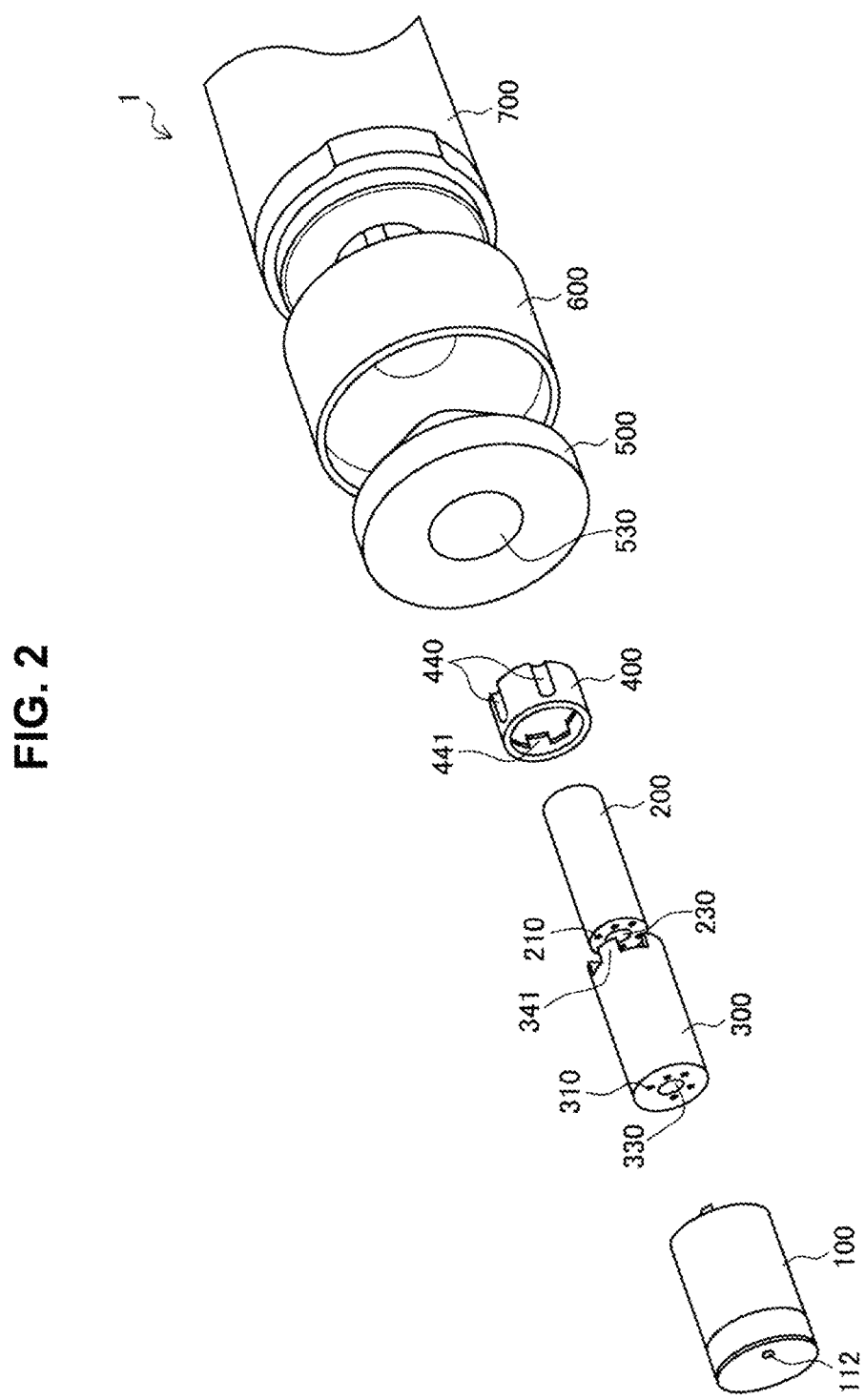
FIG. 2 is an exploded perspective view of the aroma provision device according to the embodiment.
Figure 3:
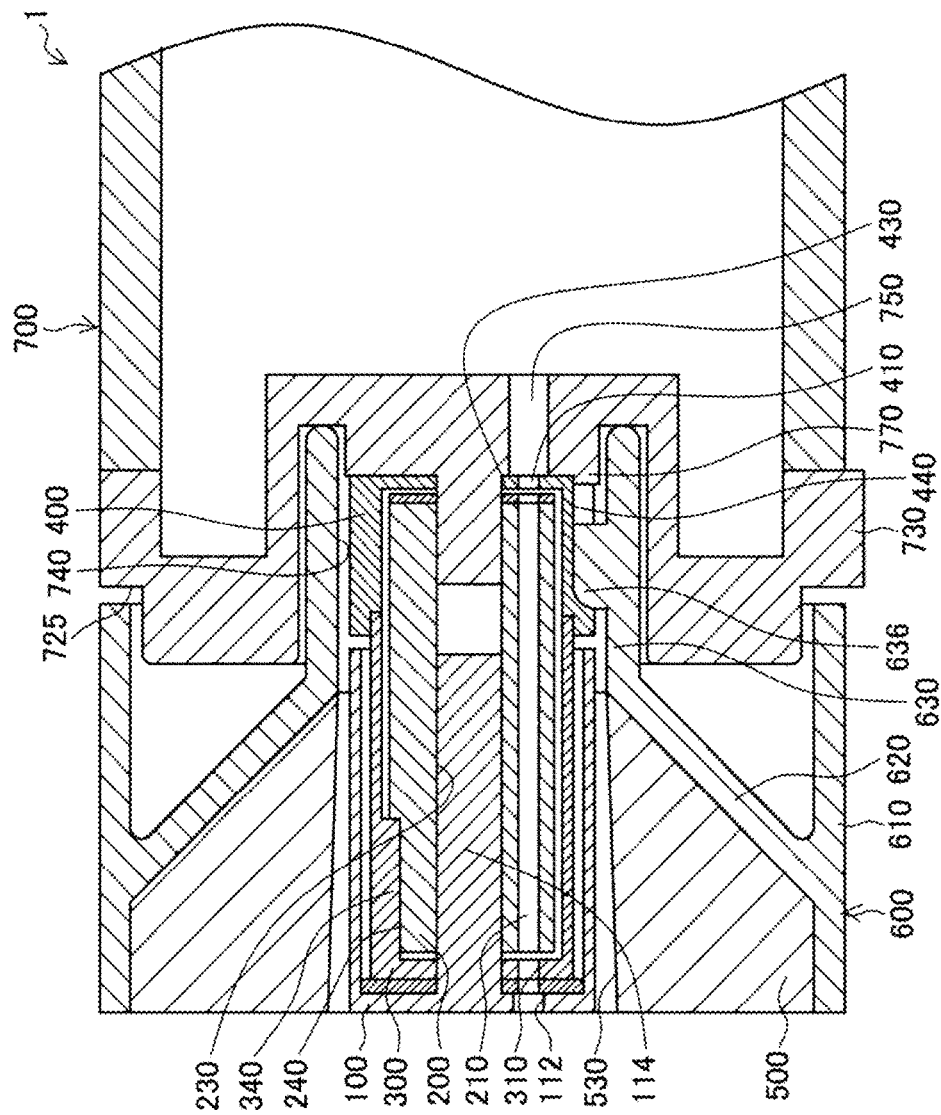
FIG. 3 is a cross-sectional view of the aroma provision device according to the embodiment in an axial direction.

Note that, the description is given in the following order.
1. Aroma provision device
2. Perfume retainer member (perfume cartridge)
3. Modifications
4. Cover and retainer protection structure
5. Perfume leakage prevention structure 1. Aroma Provision Device With reference to FIG. 1 to FIG. 3, an aroma provision device 1 according to an embodiment of the present disclosure will be described. FIG. 1 is a perspective view of the aroma provision device 1, FIG. 2 is an exploded perspective view of the aroma provision device 1, and FIG. 3 is a cross-sectional view of the aroma provision device 1 in an axial direction. Note that, in the following description, a direction in which a perfume retainer member 200 is arranged in the aroma provision device 1 is referred to as a front side, and a direction in which a base 700 is arranged in the aroma provision device 1 is referred to as a rear side.

The aroma provision device 1 according to the embodiment includes a cover 100, the perfume cartridge 200, a cartridge case 300, a prism part 500, a rotation operation part 600, and the base 700. The perfume cartridge 200 serves as the perfume retainer member. The aroma provision device 1 is a device configured to flow air into a desired air flow channel 210 selected from among a plurality of air flow channels 210 installed in the perfume cartridge 200, evaporate a perfume retained on an inner periphery of each of the air flow channels 210, and outputs the evaporated perfume. For example, the aroma provision device 1 flows air supplied from an air pump (not illustrated) into an air flow channel 210 of the perfume cartridge 200, evaporates a wet perfume, and outputs the evaporated perfume together with the air from the air flow channel 210.

For example, such an aroma provision device 1 may be used as a device for outputting aroma to a limited area. For example, the aroma provision device 1 may be used such that a user outputs aroma near his/her face one or multiple times to make himself/herself relaxed. In such a case, the aroma provision device 1 according to the embodiment does not diffuse the aroma in a wide area. Therefore, it is difficult for people around the user to smell the aroma.

The cartridge case 300 has a cylindrical shape in which a rear-side end opens among ends in the axial direction. The cartridge case 300 retains the perfume cartridge 200 therein. The cartridge case 300 has a circular opening 330 on a front-side end face. The circular opening 330 is centered on a shaft center. In addition, the cartridge case 300 has holes 310 around the opening 330. The holes 310 communicate with respective air flow channels 210 of the perfume cartridge 200.

On the inner periphery on the cartridge case 300, an engagement protrusion 340 is provided. The engagement protrusion 340 extends in the axial direction (see FIG. 3). When the perfume cartridge 200 is inserted into the cartridge case 300, the engagement protrusion 340 engages with an engagement groove 240 provided on an outer periphery of the perfume cartridge 200 (see FIG. 3). Accordingly, the perfume cartridge 200 and the cartridge case 300 are aligned, and the air flow channels 210 communicate with the holes 210. It is also possible to provide the engagement protrusion on the cartridge case 300 and provide the engagement groove on the perfume cartridge 200.

In addition, the cartridge case 300 has a plurality of claws 341 on the rear-side end (see FIG. 2). The claws 341 are formed at regular intervals by partially shifting a position of the rear-side end of the cartridge case 300 in the axial direction.

The perfume cartridge 200 has a cylindrical shape. The perfume cartridge 200 includes the plurality of air flow channels 210 through which air supplied from the air pump passes. The air pump is an example of the air blow source. In the air flow channels 210, wet perfumes are retained. The perfumes are retained such that the perfumes are attached to inner surfaces of the air flow channels 210. For example, the perfumes may be essential oils, essential oils diluted with ethanol, or the like. The number of the air flow channels 210 may be one or more. The aroma provision device 1 according to the embodiment uses the perfume cartridge 200 having five air flow channels 210. Details of the perfume cartridge 200 will be described later.

The retainer 400 has a cylindrical shape in which a front-side end opens among ends in the axial direction. The retainer 400 retains a rear-side part of the cartridge case 300. The retainer 400 has a circular opening 430 on a rear-side end face. The circular opening 430 is centered on the shaft center (see FIG. 3). In addition, the retainer 400 has holes 410 around the opening 430. The holes 410 communicate with the respective air flow channels 210 of the perfume cartridge 200 (see FIG. 3).

The rear end of the cartridge case 300 is inserted into the front-side opening of the retainer 400. The retainer 400 has a plurality of receptor recess parts 441 on its inner periphery. The receptor recess parts 441 fit the claws 341 of the cartridge case 300. The number of receptor recess parts 441 corresponds to the number of claws 341. The number of claws 341 and the number of receptor recess parts 441 are equal to the number of the air flow channels 210 of the perfume cartridge 200. This enables the retainer 400 to retain the cartridge case 300 retaining the perfume cartridge 200 in any rotation phase. Therefore, the plurality of air flow channels 210 communicate with the holes 410 of the retainer 400.

The cover 100 is attached to the outside of the cartridge case 300. The cover 100 has a cylindrical shape in which a rear-side end opens among ends in the axial direction. The cover 100 has an aroma output port 112 on its front-side end face. The aroma output port 112 is configured to communicate with any one of the plurality of air flow channels 210 of the perfume cartridge 200. Air including an evaporated perfume component passes through any air flow channel 210 of the perfume cartridge 200, and is output to an outside via the aroma output port 112. An internal diameter of the aroma output port 112 is not specifically limited. However, it is preferable that the internal diameter of the aroma output port 112 is at least an internal diameter of the air flow channel 210 or more so as not to interrupt air flowing through the air flow channel 210 of the perfume cartridge 200.

The cover 100 has a fixed shaft 114 that extends from an internal face of the front-side end face in the axial direction (see FIG. 3). The fixed shaft 114 is inserted into the opening 330 of the cartridge case 300 and an axial direction hole 230 of the perfume cartridge 200. The cover 100 is rotatable around a rotation axis relative to the cartridge case 300 retaining the perfume cartridge 200. The fixed shaft 114 serves as the rotation axis. The air flow channels 210 to communicate with the aroma output port 112 are switched depending on its relative position. A tip of the fixed shaft 114 has an engagement part (not illustrated) having a half body obtained by cutting along the shaft center. The shape of the engagement part is not limited to the shape described above. It is only necessary for the engagement part to have an attachable/detachable shape that fits a fixed shaft 760 of the base 700 (see FIG. 3).

The rotation operation part 600 is arranged outside the cover 100, the cartridge case 300, the perfume cartridge 200, and the retainer 400. The rotation operation part 600 includes an external cylinder 610, a truncated-cone-shaped part 620, and an inner cylinder 630. The internal cylinder 630 has an engagement protrusion 636 on its inner periphery. The external cylinder 610 and the internal cylinder 630 are connected via the truncated-cone-shaped part 620. A large-diameter-side end of the truncated-cone-shaped part 620 is connected with a central part of an inner periphery of the external cylinder 610 in the axial direction. In addition, a small-diameter-side end of the truncated-cone-shaped part 620 is connected with a front-side end of the inner cylinder 630. The prism part 500 is arranged in a space on the front side of the truncated-cone-shaped part 620. The prism part 500 has an axial direction hole 530 centered on the shaft center. In the axial direction hole 530, the cover 100, the cartridge case 300, and the perfume cartridge 200 are arranged.

The cover 100, the cartridge case 300, the perfume cartridge 200, and the retainer 400 are inserted into an inside of the internal cylinder 630 of the rotation operation part 600. At this time, the engagement protrusion 636 of the internal cylinder 630 is arranged in any of the plurality of engagement grooves 440 provided on the outer periphery of the retainer 400. This enables the retainer 400, and the cartridge case 300 and the perfume cartridge 200 held by the retainer 400 to rotate integrally with the rotation operation part 600. In addition, the cover 100 is rotatable relative to the rotation operation part 600 since the cover is rotatable relative to the cartridge case 300, the perfume cartridge 200, and the retainer 400.

The rotation operation part 600, the cover 100, the perfume cartridge 200, the cartridge case 300, the retainer 400, and the like are supported by the base 700. The base 700 has a recess part 740 having a circular cross section at a central part on its front-side face. The internal cylinder 630 of the rotation operation part 600 is inserted into the recess part 740. In addition, the base 700 has a ring-shaped step part 725 at an outer edge on the front-side face. On the circular step part 725, the external cylinder 610 of the rotation operation part 600 is arranged. The external cylinder 610 is arranged on the step part 725, the internal cylinder 630 of the rotation operation part 600 is arranged in the recess part 740, and the retainer 400, the perfume cartridge 200, and the like are arranged in the inside of the internal cylinder 630.

The base 700 has a fixed shaft 760 that stands on a bottom face of the recess part 740 and that extends in the front side. The fixed shaft 760 is inserted into the opening 430 of the retainer 400 and the axial direction hole 230 of the perfume cartridge 200. For example, the fixed shaft 760 is lightly pressed and inserted into the axial direction hole 230 of the perfume cartridge 200. Thereby, the rotation operation part 600, the cover 100, the perfume cartridge 200, the cartridge case 300, the retainer 400, and the like are supported by the base 700.

A tip of the fixed shaft 760 has an engagement part (not illustrated) having a half body obtained by cutting along the shaft center. In the axial direction hole 230 of the perfume cartridge 200, the engagement part of the fixed shaft 760 fits the engagement part of the tip of the fixed shaft 114 of the cover 100 while the engagement part of the fixed shaft 760 is rotated 180 degrees around the axis. Accordingly, it becomes impossible for the cover 100 to rotate relative to the base 700. Thereby, it becomes possible for the rotation operation part 600, the perfume cartridge 200, the cartridge case 300, and the retainer 400 to rotate relative to the base 700. Note that, in a way similar to the engagement part of the cover 100, the shape of the engagement part of the fixed shaft 760 is not limited to the shape described above. It is only necessary for the engagement part of the fixed shaft 760 to have an attachable/detachable shape that fits the fixed shaft 114 of the cover 100.

In addition, the base 700 has an air supply port 750 on the bottom face of the recess part 740. The base 700 includes an air pump, a battery, a circuit board, and the like (that are not illustrated) therein. The air pump is an example of the air blow source. The air pump is driven by electric power supplied from the battery, and introduces air into the air supply port 750. For example, the air pump may be a diaphragm pump configured to suction and pump air by supplying alternating current to a piezoelectric element and deforming a diaphragm. The battery may be a replaceable electric battery capable of discharging only or may be a secondary battery capable of charging and discharging. The driving of the air pump is turned on and off by operating a switch operation part 730. For example, when the switch operation part 730 is pressed, a switching element of the circuit board is electrically connected, and electric power is supplied from the battery to the air pump. This enables to supply air to the perfume cartridge 200 via the air supply port 750.

For example, the electric power distribution may be turned on or off every time the switch operation unit 730 is pressed. Alternatively, the electric power distribution is kept in the ON state while the switch operation part 730 is being pressed. On the circuit board, another electronic component such as a light source like a light emitting diode (LED) for showing operation states of the aroma provision device 1 may be mounted. In addition, it is also possible to mount a communication device on the circuit board to enable the aroma provision device 1 to be operated by a remote controller, a smartphone, or the like.

Note that, the air blower configured to supply air to the perfume cartridge 200 is not limited to the air pump. For example, the air blower may be an air blower with rotating blades. In addition, the air blower configured to supply air to the perfume cartridge 200 may be an electric air blower or may be a manual air blower. In the case where the manual blower is used as an air supplying means, the battery, the switch operation part 730, and the circuit board may be omitted.

In addition, a protrusion 770 for position alignment is provided on the bottom face of the recess part 740. The protrusion 770 fits into the engagement groove 440 of the retainer 400 in which the engagement protrusion 636 of the rotation operation part 600 is arranged. On the outer periphery of the retainer 400, the engagement grooves 440 are provided at regular intervals. The number of the engagement grooves 440 is the same as the number of air flow channels 210 of the perfume cartridge 200. The air supply port 750 communicates with any of the air flow channels 210 in a state where the protrusion 770 fits into any of the engagement grooves 440. Therefore, it is possible to switch the air flow channels 210 to be communicated with the air supply port 750 by rotating the rotation operation part 600.

The protrusion 770 may be biased to the front side by using a spring or the like. In other words, while rotating the perfume cartridge 200, the spring may be compressed, for example, and the protrusion 770 may be recessed. When any of the engagement grooves 440 fits the position of the protrusion 770, the protrusion 770 may protrude toward the engagement groove 440. Thereby, it is possible to rotate the retainer 400, the rotation operation part 600, and the like without changing a distance between the base 700 and the retainer 400, etc.

Figure 4:
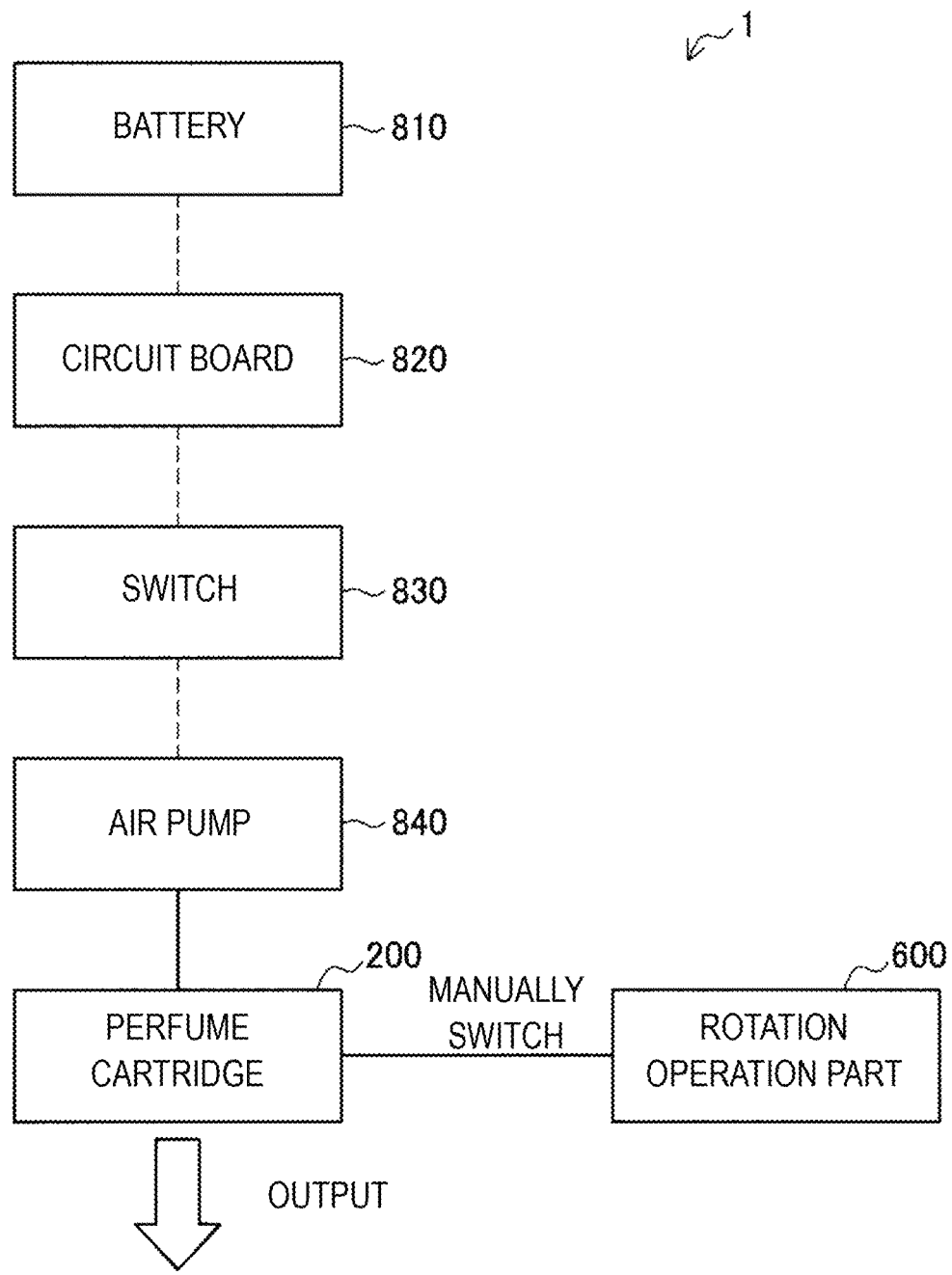
FIG. 4 is a block diagram illustrating an example of a system configuration of the aroma provision device according to the embodiment.

FIG. 4 is a block diagram illustrating an example of a system configuration of the aroma provision device 1. A battery 810 is electrically connected with an air pump 840 via a circuit board 820 and a switching element 830. In response to operation performed on the switch operation part 730, electric power of the battery 810 is supplied to the air pump 840. When the air pump 840 is driven and air flows into the air flow channel 210 of the perfume cartridge 200, a perfume retained on an inner face of the air flow channel 210 is evaporated, and aroma is output with the air. In addition, in an example illustrated in FIG. 18, the rotation operation part 600 is capable of being manually rotated, and it is possible to switch the air flow channels 210 of the perfume cartridge 200 into which air supplied from the air pump 840 is introduced.

Figure 5:
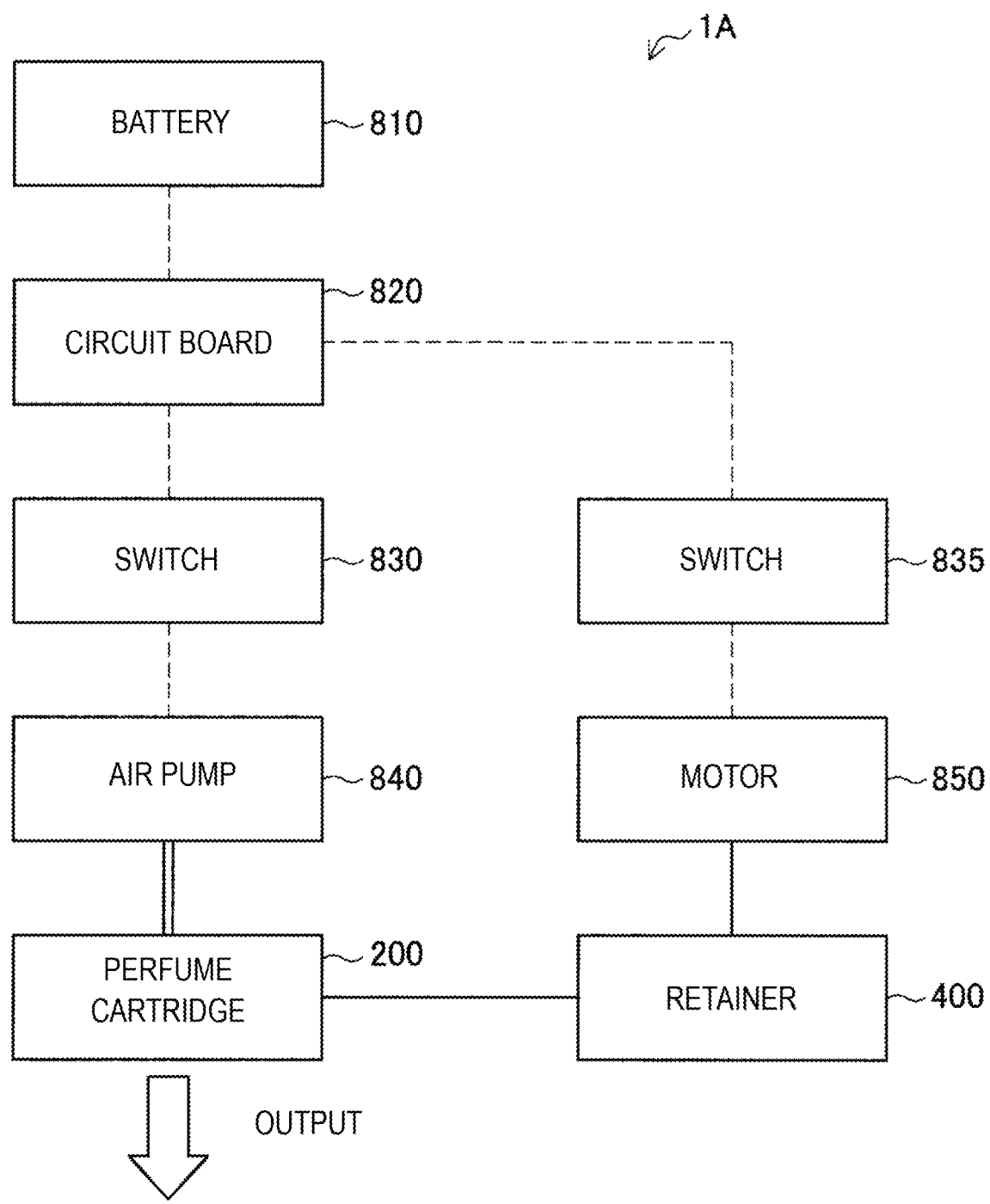
FIG. 5 is a block diagram illustrating another example of a system configuration of the aroma provision device according to the embodiment.

FIG. 5 is a block diagram illustrating a system configuration of another aroma provision device 1A. In the example illustrated in FIG. 5, the rotation operation part 600, the cartridge case 300, or the retainer 400 is capable of being rotated by a motor 850, and it is possible to switch the air flow channels 210 of the perfume cartridge 200 into which air supplied from the air pump 840 is introduced.

2. Perfume Retainer Member (Perfume Cartridge)

Figure 6:
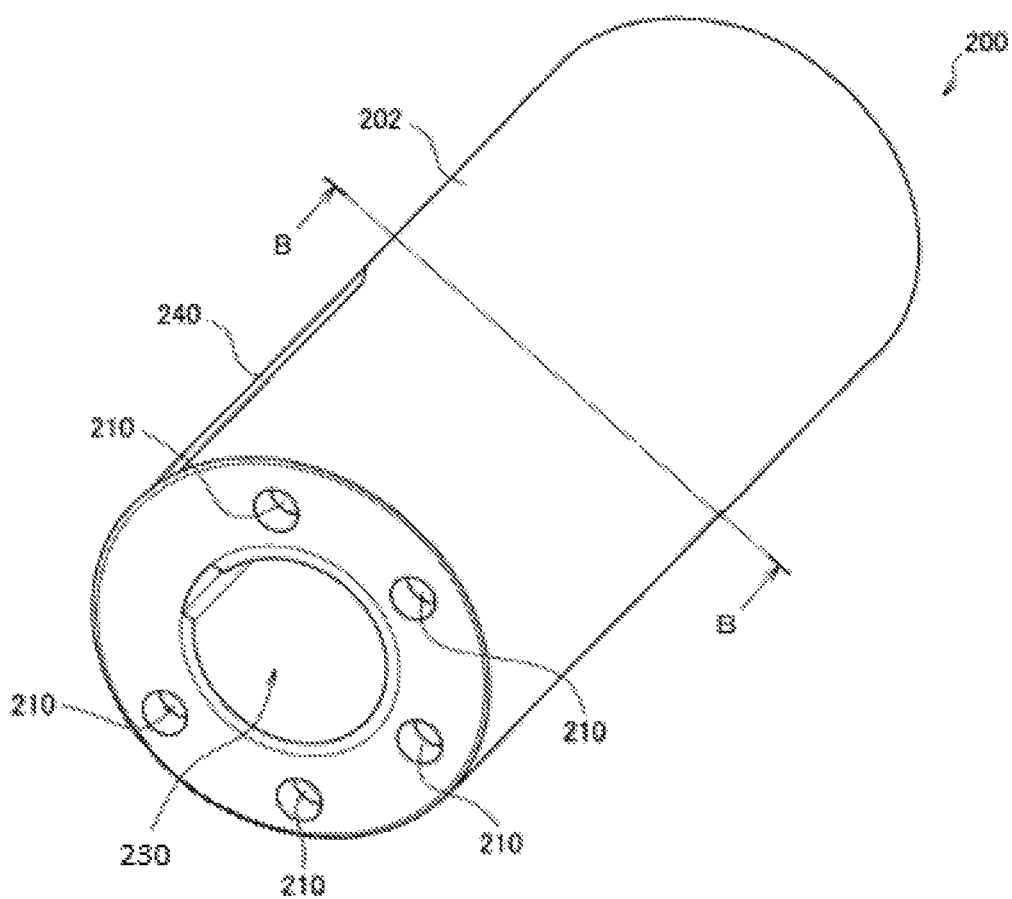
FIG. 6 is a perspective view illustrating an example of a configuration of a perfume cartridge according to the embodiment.
Figure 7:
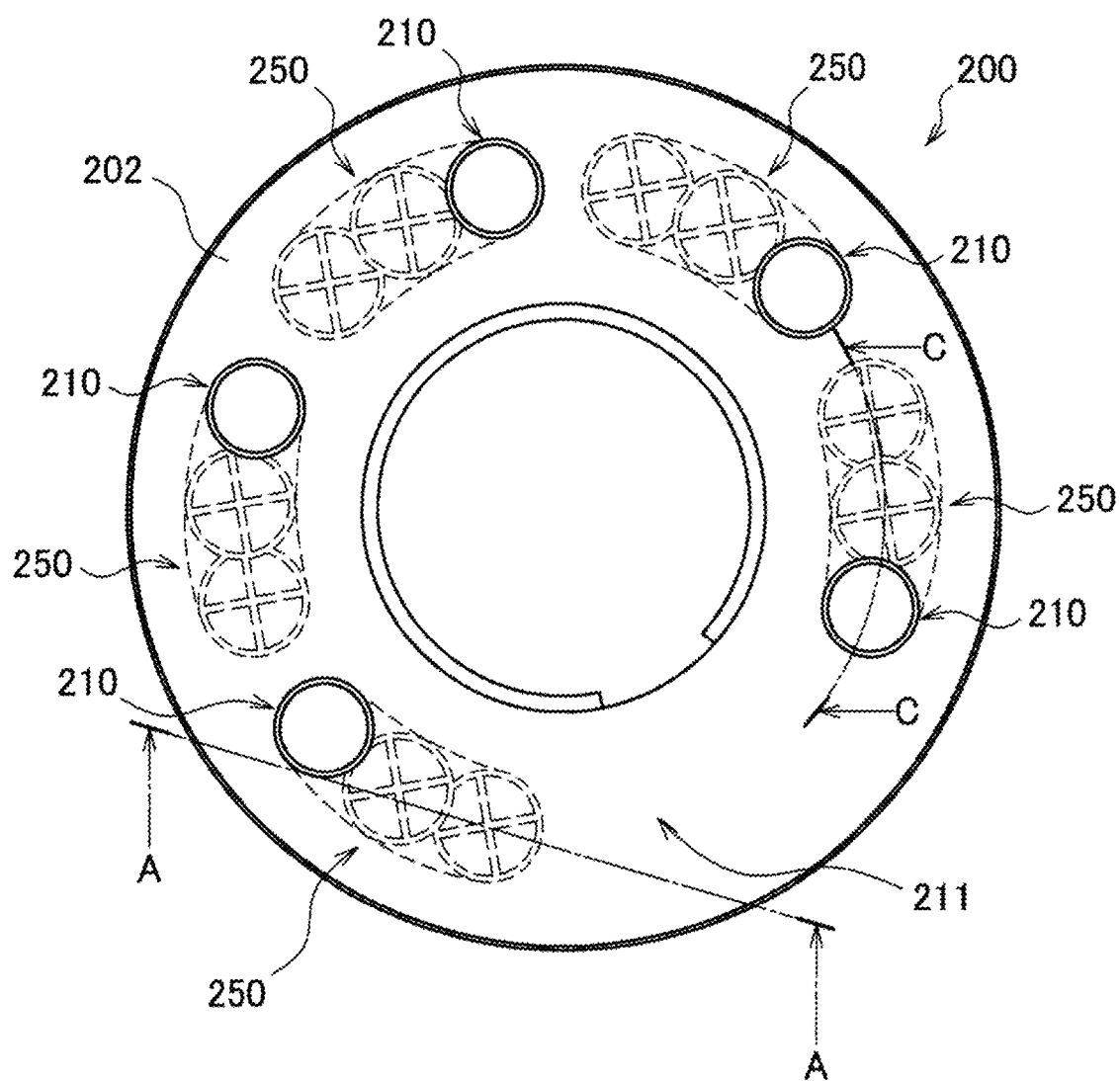
FIG. 7 is a front view of the perfume cartridge according to the embodiment seen from the axial direction.
Figure 8:
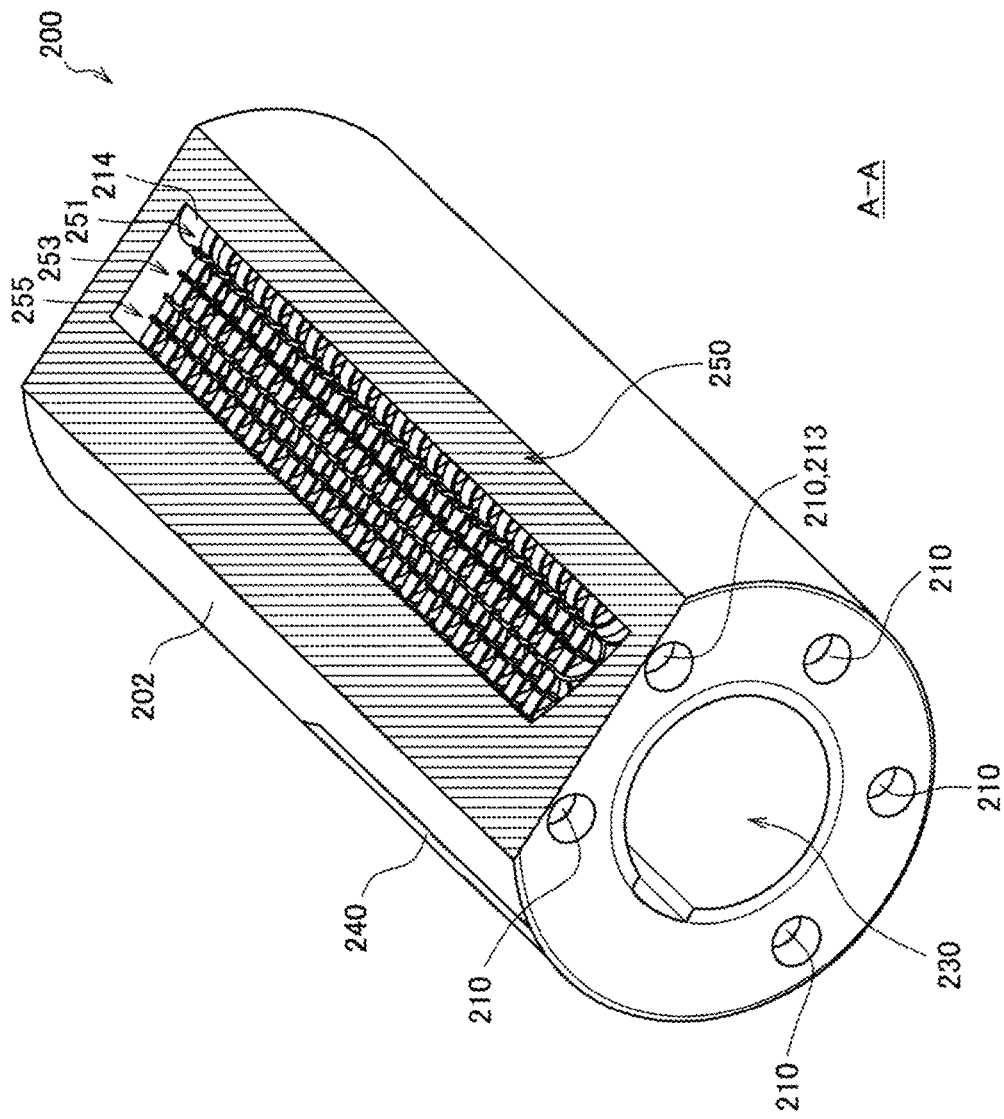
FIG. 8 is a perspective view including an A-A cross section of the perfume cartridge illustrated in FIG. 7.
Figure 9:
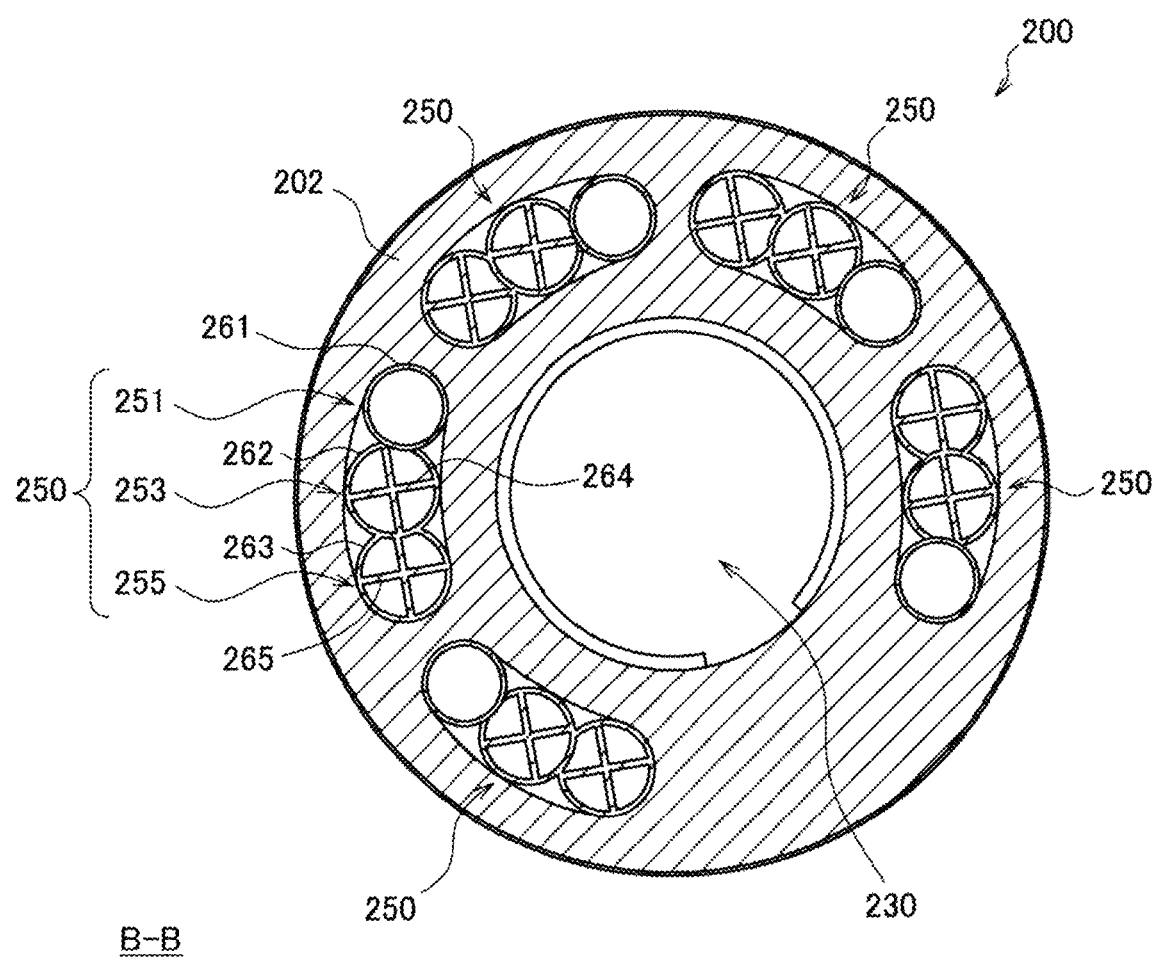
FIG. 9 is a cross-sectional view of the perfume cartridge taken along a line B-B in FIG. 6.
Figure 10:
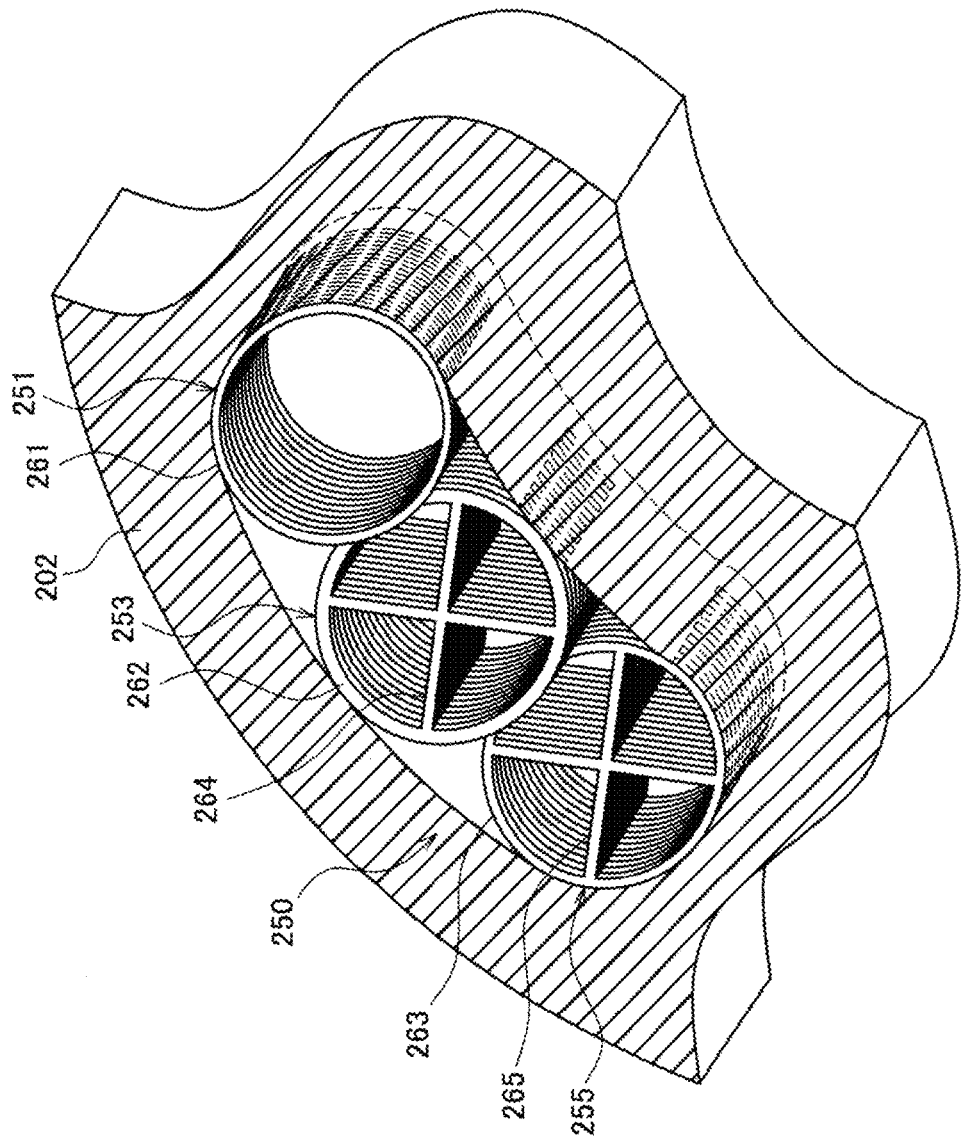
FIG. 10 is a perspective view illustrating a configuration of a retainer space of the perfume cartridge according to the embodiment.
Figure 11:
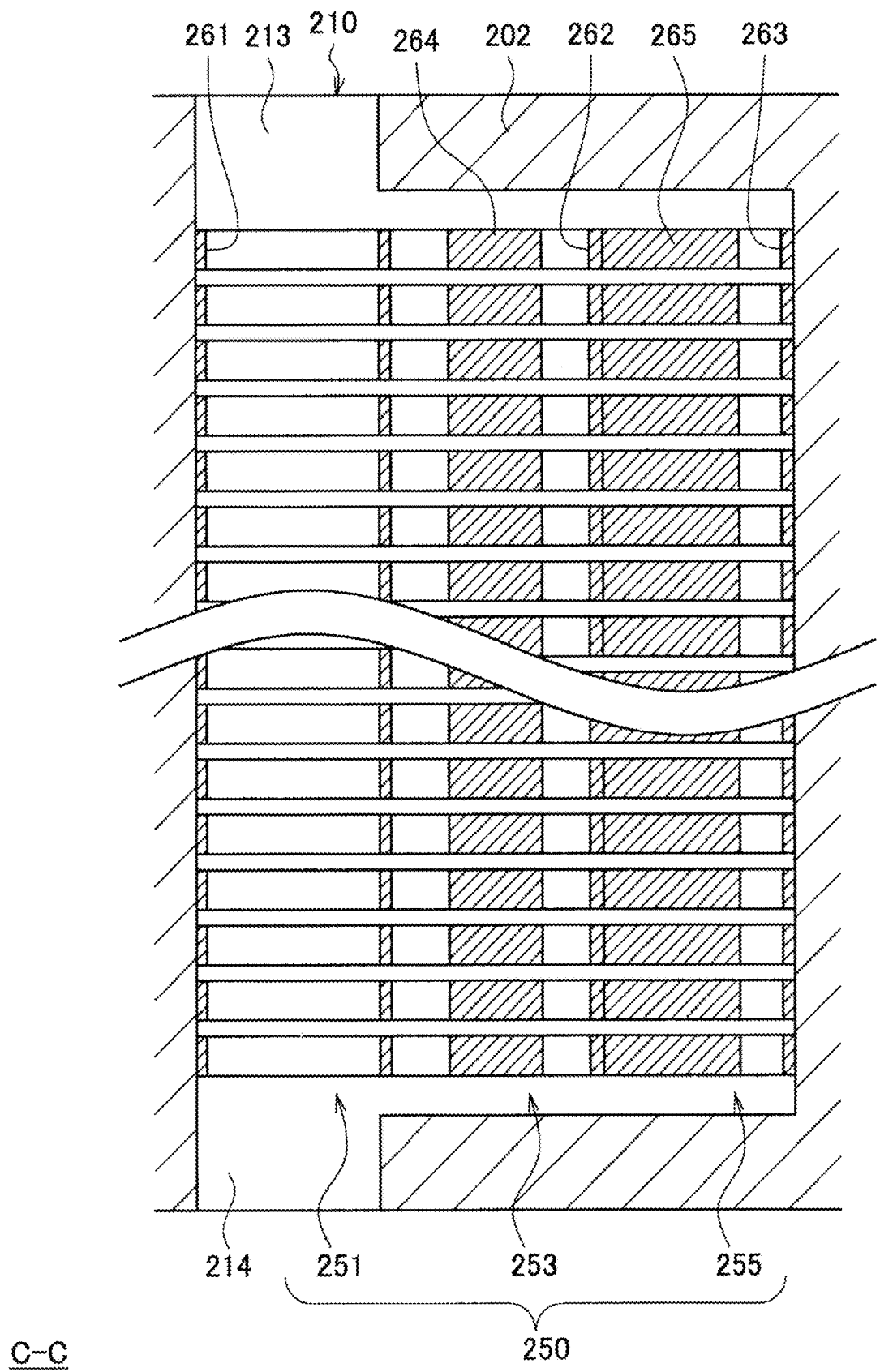
FIG. 11 is a cross-sectional view of an air flow channel of the perfume cartridge taken along a line C-C in FIG. 7.

Next, with reference to FIG. 6 to FIG. 11, the perfume cartridge 200 serving as the perfume retainer member used in the aroma provision device 1 will be described. FIG. 6 is a perspective view of the perfume cartridge 200, and FIG. 7 is a side view of the perfume cartridge seen from the radial direction. In addition, FIG. 8 is a perspective view including an A-A cross section of the perfume cartridge 200 illustrated in FIG. 7, and FIG. 9 illustrates a B-B cross section of FIG. 6. In addition, FIG. 10 is a perspective view illustrating a retainer space 250, and FIG. 11 is a schematic diagram illustrating a configuration of the air flow channel 210. FIG. 11 illustrates a C-C cross section of the air flow channel 210.

The perfume cartridge 200 includes a main body 202, the axial direction hole 230, and the plurality of air flow channels 210. The main body 202 has a cylindrical shape. The main body 202 has the axial direction hole 230 centered on the shaft center. The axial direction hole 230 may be used as a guide when attaching the cover 100 and the base 700. Note that, the shape of the perfume cartridge 200 is not limited to the cylindrical shape. For example, the shape of the perfume cartridge 200 may be a cylinder shape without a central hole, a rectangular cuboid shape, a cubic shape, or other appropriate shapes.

The wet perfume is attached to at least a part of the inner face of each air flow channel 210 and retained therein. The wet perfume may be an essential oil or a liquid obtained by diluting the essential oil with ethanol. For example, the liquid perfume is charged in the air flow channel 210, and then high-pressure gas such as air is supplied to the inside of the air flow channel 210 for a predetermined time. Therefore, the redundant liquid perfume is spewed, and it is possible to attach the wet perfume to the inner surface of the air flow channel 210. In the perfume cartridge 200 according to the embodiment, the wet perfume is not charged in the air flow channels 210. Therefore, there is no possibility of leakage of the wet perfume from the perfume cartridge 200.

The air flow channels 210 are arranged around the shaft center of the main body 202 at regular intervals. Accordingly, it is possible to switch the air flow channels 210 to which air is blown, by rotating the perfume cartridge 200 around the axis by a constant rotation angle. The perfumes retained in the respective air flow channels 210 may be the same, or a part or all of the perfumes retained in the respective air flow channels 210 may be different from each other. In the case where the same perfumes are retained in the respective air flow channels 210, a user can enjoy his/her favorite aroma over a long period. Alternatively, in the case where different perfumes are retained in the respective air flow channels 210, it is possible to switch aromas to be output by switching an air supply destination between the air flow channels 210. Therefore, for example, it is possible to switch the aromas depending on his/her feelings.

In the perfume cartridge 200 according to the embodiment, five air flow channels 210 are arranged at regular intervals of 60°, and one air flow channel is omitted. The position of the part 211 at which the air flow channel is not formed is aligned with the position of the aroma output port 112 of the cover 100 while the aroma provision device 1 is not used to keep the aroma trapped in the perfume cartridge 200. Note that, the number of air flow channels 21 is not limited to five.

For example, the main body 202 of the perfume cartridge 200 may include an organic polymeric material so as to make the perfume including an essential oil or the like easy to infiltrate. For example, as the organic polymeric material, any one of or a mixture of polyvinyl chloride, polyethylene, phenolic resin, olefin resin, nylon, polyester, synthetic rubber, silicone resin, natural rubber, protein, nucleic acid, lipid, and polysaccharide may be used. However, the main body 202 is not limited to the above described examples. For example, one or a plurality of materials may be used among polymeric resin such as acrylic resin, urethane resin, ABS resin, polyether ether ketone (PEEK) resin, polyacetal (POM) resin, fluorocarbon polymer, cycloolefin polymer resin, or polyimide resin, metal such as stainless steel or aluminium, inorganic crystal such as quartz, and glass.

Note that, for example, the perfume cartridge 200 may be manufactured by using a 3D printer, and a material suitable for 3D printing may be selected as the material of the perfume cartridge 200.

The perfume cartridge 200 has the engagement groove 240 on the outer periphery of the main body 202. The engagement groove 240 is used for position alignment between the cartridge case 300 and the perfume cartridge 200 in addition to the engagement protrusion 340 provided on the inner periphery of the cartridge case 300. In addition, by fitting the engagement protrusion 340 into the engagement groove 240, in becomes impossible for the cartridge case 300 to rotate relative to the perfume cartridge 200, and it is possible to rotate the cartridge case 300 integrally with the perfume cartridge 200.

Each of the air flow channels 210 has the retainer space 250 made in the main body 202, and a first opening 213 and a second opening 214 configured to open the retainer space 250 to an outside of the main body 202. Most of the perfume is mainly retained in the retainer space 250 while the most of the perfume is attached to the inner surface of the retainer space 250 in a wet state. The first opening 213 and the second opening 214 are provided on the respective end faces of the main body 202 in the axial direction. The first opening 213 is an inlet configured to introduce air into the retainer space 250, and the second opening 214 is an outlet configured to output air including an aroma component from the retainer space 250. At least one of the first opening 213 and the second opening 214 may be provided on the outer periphery of the main body 202.

In the perfume cartridge 200 according to the embodiment, the wet perfume is retained on the inner periphery of the air flow channel 210. Therefore, the first opening 213 and the second opening 214 do not have to have a function of preventing leakage of a liquid perfume. However, if at least one of the first opening 213 and the second opening 214 has a too small internal diameter, a pressure drop at a time of blowing air into the air flow channel 210 may get larger. Therefore, it is preferable that sizes of the internal diameters of the first opening 213 and the second opening 214 fall within a range from 500 to 3000 μm, for example.

In addition, the retainer space 250 in the air flow channel 210 is made such that a large surface area to which the perfume is attached can be obtained. The retainer space 250 in the perfume cartridge 200 according to the embodiment includes a plurality of segment regions 251, 253, and 255 combined with each other (see FIG. 8 to FIG. 10). Each of the segment regions 251, 253, and 255 has a diameter of 3000 μm or less. A flow channel having an internal diameter of several tens to hundreds of μm of its cross section is also referred to as a "micro flow channel". As the internal diameters of the respective segment regions 251, 253, and 255 get smaller, it becomes difficult for turbulence to occur in air flowing in the respective segment regions 251, 253, and 255, and the air flow tends to become laminar flow.

In addition, in the case where the output of the air pump is constant, air flow speed in the air flow channel 210 gets faster as the internal diameters of the respective segment regions 251, 253, and 255 get smaller. This can improve straightness of a flow of air output from the aroma output port 112 in the aroma provision device 1 according to the embodiment. The air includes the aroma component. Therefore, by outputting the air including the aroma component to the user of the aroma provision device 1, it is possible to provide aroma to the user without affecting surroundings of the user.

In addition, the segment regions 251, 253, and 255 with such internal diameters are capable of stably retaining small amounts of perfumes by attaching the wet liquid perfumes on their inner surfaces. This can extend duration of use of the perfume cartridge 200 without dropping a perfume every time the aroma provision device 1 is used.

In addition, when the retainer space 250 in which the segment regions 251, 253, and 255 with relatively small internal diameters are combined is used, it is possible to obtain a high ratio of the surface area to a volume in the retainer space 250, and it is possible to output air with an evaporated perfume in high concentration by using a small amount of perfume. In addition, by using the retainer space 250 in which the segment regions 251, 253, and 255 with relatively small internal diameters are combined, it is possible to obtain the perfume cartridge 200 with a smaller shape even in the case where the perfume cartridge 200 includes the plurality of air flow channels 210. Therefore, it is possible to carry the perfume cartridge 200 and the aroma provision device 1 easily.

With reference to FIG. 9 to FIG. 11, details of the configuration example of the retainer space 250 will be described. The shape of the retainer space 250 on the cross section of the perfume cartridge 200 in a circumferential direction is a substantially oval shape. The retainer space 250 with the substantially oval shape is segmented into three segment regions 251, 253, and 255 that extend in the axial direction of the perfume cartridge 200. In other words, the three segment regions 251, 253, and 255 are arranged in parallel with each other in the axial direction of the perfume cartridge 200. The first opening 213 and the second opening 214 are provided on an extension of the first segment region 251 among these three segment regions.

The first segment region 251 is positioned at one end side in a longitudinal direction of the oval-shaped cross section of the retainer space 250. The first segment region 251 has a plurality of ring-shaped surface increase parts 261 that are arranged in the axial direction. The ring-shaped surface increase parts 261 are structural parts for increasing an internal surface area of the retainer space 250. A part of the ring-shaped surface increase part 261 is connected with the inner face of the retainer space 250.

The second segment region 253 is positioned at a center of the oval-shaped cross section of the retainer space 250 in the longitudinal direction. The second segment region 253 has a plurality of ring-shaped surface increase parts 262 that are arranged in the axial direction, and a plurality of cross-shaped surface increase parts 264 formed on the inner periphery part of the respective ring-shaped surface increase parts 262. A part of the ring-shaped surface increase parts 262 of the second segment region 253 is connected with the inner face of the retainer space 250, and the other parts are integrated with the ring-shaped surface increase parts 261 of the first segment region 251.

In addition, for example, the cross-shaped surface increase parts 264 are formed along cross sections that are perpendicular to the axis of the perfume cartridge 200, such that four unit radii are connected at an approximate center of the second segment region 253. The cross-shaped surface increase part 264 may include a plurality of the unit radii obtained by rotating the unit radius extending in the radial direction from the shaft center of the second segment region 253 by a predetermined rotation angle (such as 90°). Ends of the respective unit radii may be connected with the inner periphery of the ring-shaped surface increase part 262.

The intervals between the ring-shaped surface increase parts 262 and the cross-shaped surface increase parts 264 arranged in the axial directions are the same as the intervals between the ring-shape surface increase parts 261 of the first segment region 251. Therefore, gaps between the adjacent ring-shaped surface increase parts 261 arranged in the first segment region 251 in the axial direction are communicated with gaps between the adjacent ring-shaped surface increase parts 262 arranged in the second segment region 253 in the axial direction.

The third segment region 255 is positioned at the other end side in the longitudinal direction of the oval-shaped cross section of the retainer space 250. In a way similar to the second segment region 253, the third segment region 255 has a plurality of ring-shaped surface increase parts 263 that are arranged in the axial direction, and a plurality of cross-shaped surface increase parts 265 formed on the inner periphery part of the respective ring-shaped surface increase parts 263. A part of the ring-shaped surface increase parts 263 of the third segment region 255 is connected with the inner face of the retainer space 250, and the other parts are integrated with the ring-shaped surface increase parts 262 of the second segment region 253. In addition, ends of the respective unit radii of the cross-shaped surface increase part 265 are connected with the inner periphery of the ring-shaped surface increase part 263.

The intervals between the ring-shaped surface increase parts 263 and the cross-shaped surface increase parts 265 arranged in the axial directions are the same as the intervals between the ring-shape surface increase parts 261 of the first segment region 251, or are the same as the intervals between the ring-shaped surface increase parts 262 and the cross-shaped surface increase parts 264 of the second segment region 253. Therefore, gaps between the adjacent ring-shaped surface increase parts 262 arranged in the second segment region 253 in the axial direction are communicated with gaps between the adjacent ring-shaped surface increase parts 263 arranged in the third segment region 255 in the axial direction.

For example, a width of each of the ring-shaped surface increase parts 261, 262, and 263 or each of the cross-shaped surface increase parts 264 and 265 (a length in the axial direction) may be 5 to 1000 µm. In addition, a thickness of each of the ring-shaped surface increase parts 261, 262, and 263 or each of the cross-shaped surface increase parts 264 and 265 (a length in the direction perpendicular to the axial direction) may be 5 to 500 µm.

Such ring-shaped surface increase parts 261, 262, 263, and such cross-shaped surface increase parts 264, and 265 are capable of keeping spaces through which air passes so as not to interrupt flux, and increasing a surface area of the inner face of the retainer space 250. Therefore, since the liquid perfume is attached to the surface, it is possible to increase an amount of wet perfumes retained in the air flow channels 210 against gravity and air flow, by using its wet property, surface tension, and chemical interaction on its interface. This can extend duration of use of the perfume cartridge 200. In the perfume cartridge 200 according to the embodiment, the surface areas of the inside of the second segment region 253 and the inside of the third segment region 255 are larger than the surface area of the inside of the first segment region 251. Therefore, each of the second segment region 253 and the third segment region 255 is capable of retaining a larger amount of perfume than the first segment region 251.

In addition, in the perfume cartridge 200 according to the embodiment, a ratio of a volume of the ring-shaped surface increase parts 261 to whole capacity of the first segment region 251 is smaller than ratios of volumes of the ring-shaped surface increase parts 262 and the cross-shaped surface increase parts 264 to whole capacity of the second segment region 253. In addition, ratios of the volumes of the ring-shaped surface increase parts 262 and the cross-shaped surface increase parts 264 to the whole capacity of the second segment region 253 are similar to ratios of volumes of the ring-shaped surface increase parts 263 and the cross-shaped surface increase parts 265 to whole capacity of the third segment region 255. Therefore, the segment regions 251, 253, and 255 have different pressure drops from each other when air is blown.

In specific, the first segment region 251 has a pressure drop smaller than the second segment region 253 and the third segment region 255 when air is blown. Therefore, it is easy for the air to flow in the first segment region 251 in comparison with the second segment region 253 and the third segment region 255. Therefore, a part or all of air introduced into the air flow channel 210 via the first opening 213 passes through the second segment region 253 and the third segment region 255, and the air is output via the second opening 214 while some of the air returns into the first segment region 251 having a smaller pressure drop. This can increase concentration of the aroma component in the air.

In addition, the first segment region 251, the second segment region 253, and the third segment region 255 communicate with each other via a plurality of gaps. Therefore, there is no part with very small cross-sectional area in the retainer space 250 as a whole. Accordingly, it is possible to suppress a pressure drop of air passing through the retainer space 250. In addition, the first opening 213 and the second opening 214 that connect the retainer space 250 with an outside of the main body 202 have relatively large internal diameters. Therefore, it is possible to ensure an amount of flow of air including an aroma component in high concentration, thereby outputting the aroma efficiently.

The air flow channels 210 may be straight in the axial direction of the perfume cartridge, or may tilt from the axial direction. However, if the length of a flow channel from the first opening 213 to the second opening 214 is too long, sometimes a pressure drop of air passing therethrough becomes large. Therefore, it is preferable that the air flow channels 210 are as straight as possible in the axial direction of the perfume cartridge 200.

Note that, the unit radius extending directions are the same between the cross-shaped surface increase parts in the respective retainer spaces 250 in the five air flow channels 210 in the perfume cartridge 200 according to the embodiment. However, the unit radius extending directions may be different from each other between the air flow channels 210 or between the segment regions. In addition, in the perfume cartridge 200 according to the embodiment, each of the cross-shaped surface increase parts 264 and 265 has a cross shape including the four unit radii. However, the number of the unit radii is not limited to four. For example, the appropriate number of unit radii may be arranged at regular intervals (for example, eight unit radii are arranged by a rotation angle of 45°). Alternatively, the cross-shaped surface increase part may be rotated at appropriate intervals.

Such surface increase parts are capable of keeping spaces through which air passes so as not to interrupt flux, and increasing surface areas of the inner faces of the air flow channels 210. Therefore, since the liquid perfume is attached to the surface, it is possible to increase an amount of perfume retained in the air flow channel 210 against gravity and air flow, by using its wet property, surface tension, and chemical interaction on its interface.

The surface increase parts in the air flow channels 210 are not limited to the ring-shaped surface increase part or the cross-shaped surface increase part. The surface increase parts in the air flow channels 210 may have any flat shape. Note that, it is possible to retain the perfumes at an equal density in the respective segment regions 251, 253, and 255 since the planar shape of the surface increase part is rotational symmetry or point symmetry around an axis of each of the segment regions.

In addition, in the case where the plurality of surface increase parts are arranged in the axial direction in each of the segment regions 251, 253, and 255, it is possible to arrange the surface increase parts such that the surface increase parts are translational symmetry in the axial direction of the air flow channel 210. Alternatively, in the case where the plurality of surface increase parts are arranged in the axial direction, it is possible to arrange the surface increase parts such that the surface increase parts are reflection symmetry with respect to any axis. However, the plurality of surface increase parts do not have to be arranged in the translational symmetry manner or the reflection symmetry manner. It is possible to arrange the plurality of surface increase parts in any form and in any manner unless the pressure drops of the flowing air are increased significantly.

In addition, the direction of the second opening 214 of the air flow channel 210 may be parallel to the axial direction of the main body 202, or may have any other angles. In addition, the cross-sectional shapes of the air flow channels 21 are not specifically limited as long as it is possible to retain the liquid perfumes attached to their inner faces and it is possible to flow air in the air flow channels 210. The cross-sectional shapes of the air flow channels 210 may be a circular shape, an oval shape, a square shape, a rectangular shape, or any other shapes, for example.

In addition, in the case where the aroma provision device 1 is used as a device to be used by an individual to enjoy aromas, it is possible to improve straightness of flow of the output aromas so as not to diffuse the output aromas in a wide area. For example, spiral grooves may be made on the inner peripheries of the air flow channels 210. If the air flow channels 210 have the spiral grooves, it is possible to improve the straightness of flow of air output via the air flow channels 210 due to the gyro effect. Alternatively, it is possible to provide a tapered part on an output opening of the air flow channel 210. The tapered part has diameters gradually narrowing towards an opening end. Since the output opening has such a tapered part, it is possible to increase flow speed of air to be output, and improve its straightness.

The first opening 213, the second opening 214, or the retainer space 250 including the first segment region 251, the second segment region 253, and the third segment region 255 with such tiny internal diameters may be formed by using an additive fabrication method and the 3D printer, for example. This enables to obtain the perfume cartridge 200 easily even in the case where the internal diameters of the segment regions 251, 253, 255, the first openings 213 and 214, or structural parts of the surface increase parts have a tiny size in units of micro.

3. Modifications

The example of the perfume cartridge 200 has been described above. However, the configuration of the air flow channels 210 of the perfume cartridge 200 is not limited to the above described example. Next, several modifications of the perfume cartridge with different types of air flow channels will be described.

3-1. First Modification

Figure 12:
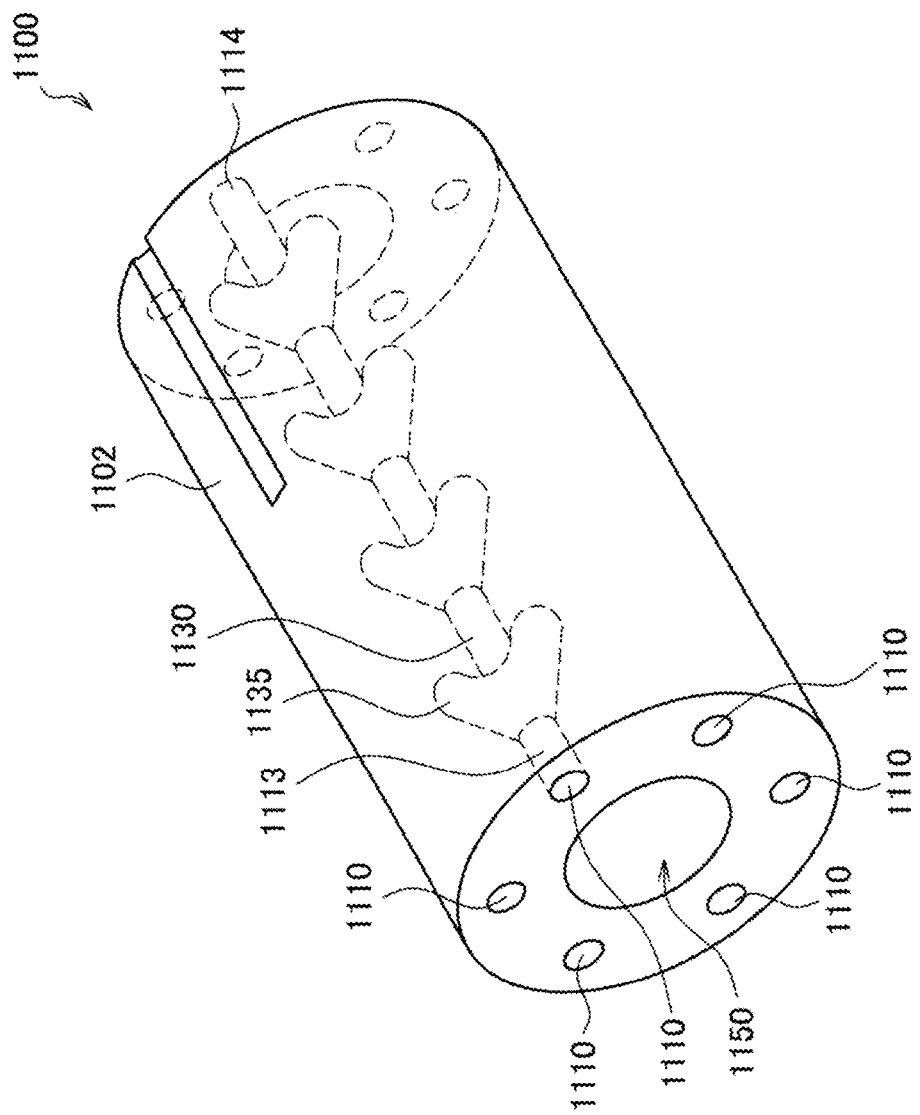
FIG. 12 is a perspective view of a perfume cartridge according to a first modification.
Figure 13:
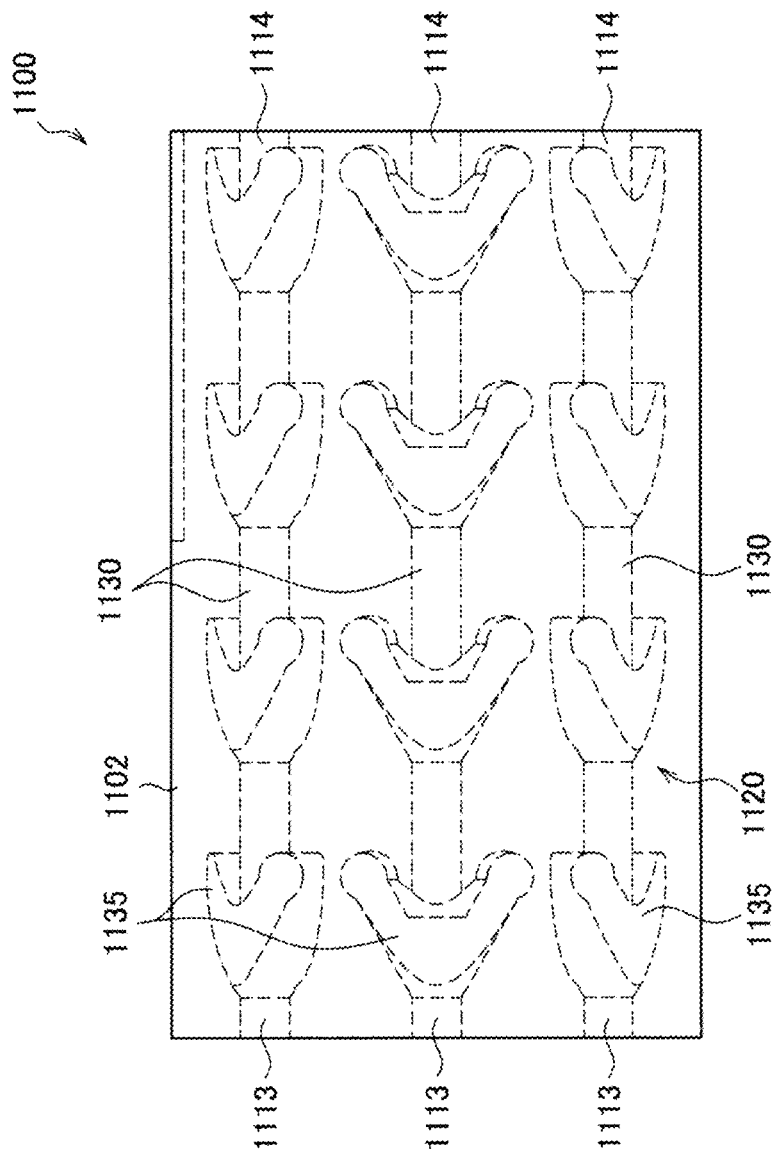
FIG. 13 is a side view of the perfume cartridge according to the first modification seen from a radial direction.
Figure 14:
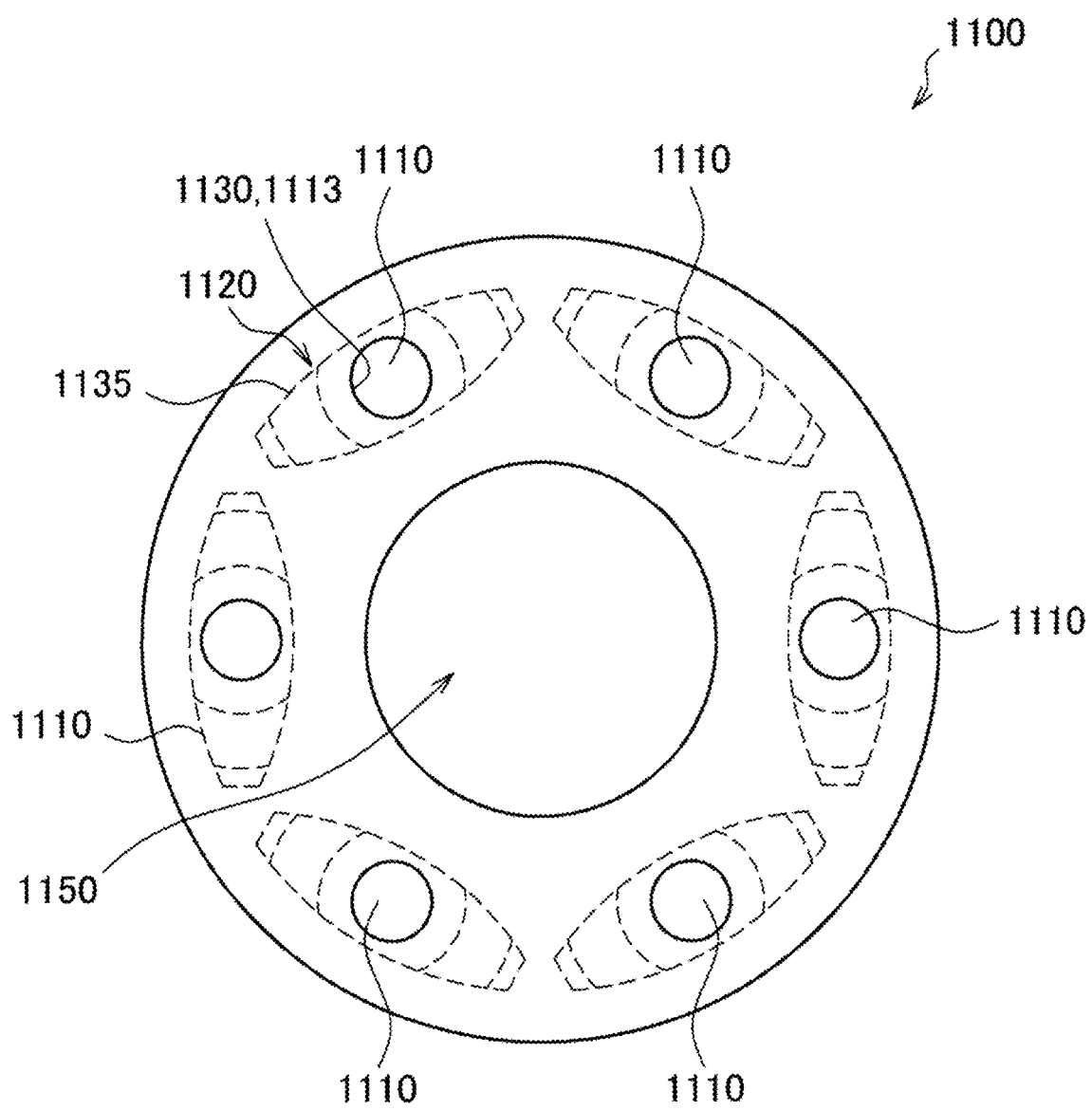
FIG. 14 is a side view of the perfume cartridge according to the first modification seen from the axial direction.
Figure 15:
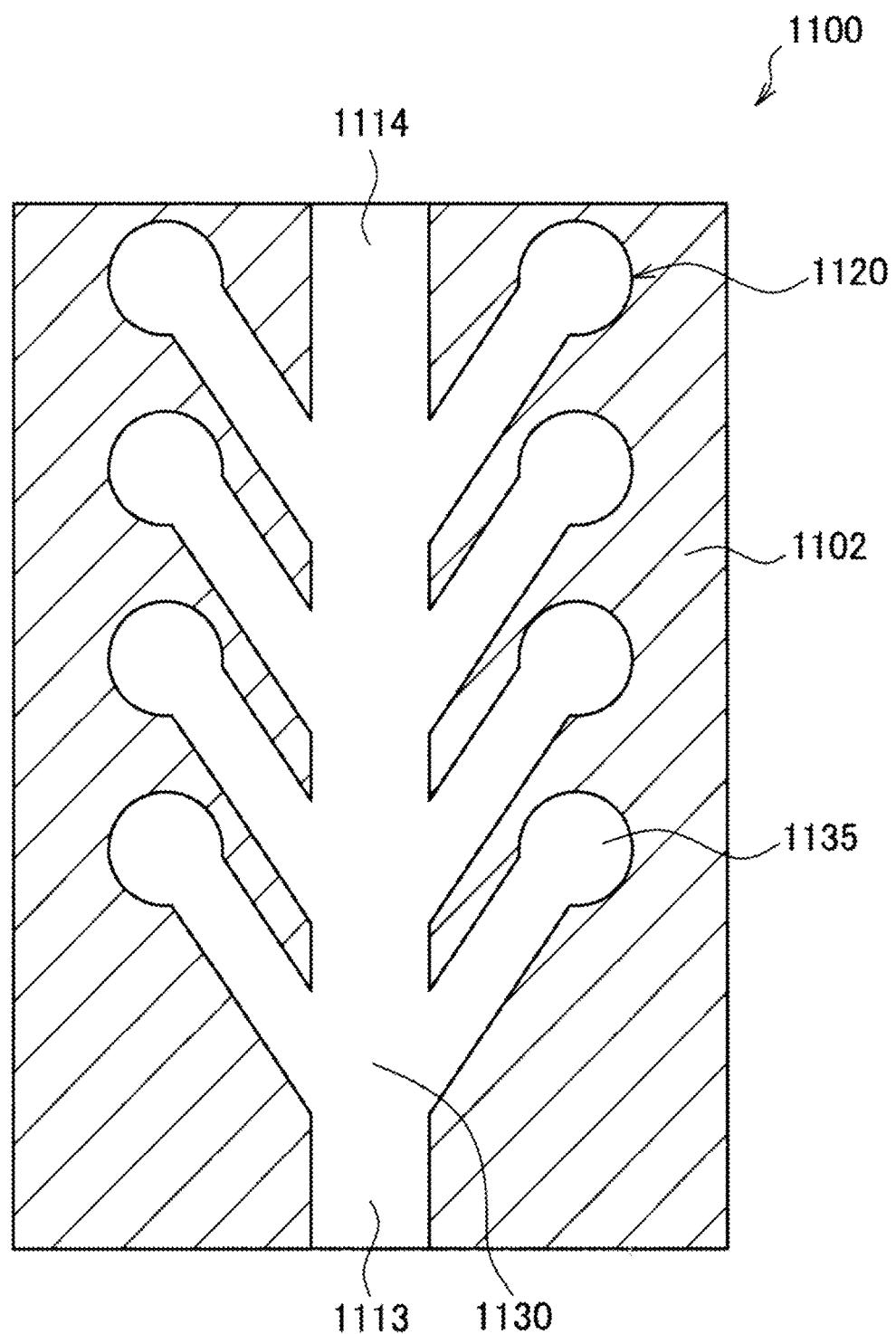
FIG. 15 is a schematic diagram illustrating a configuration of an air flow channel of the perfume cartridge according to the first modification.
Figure 16:
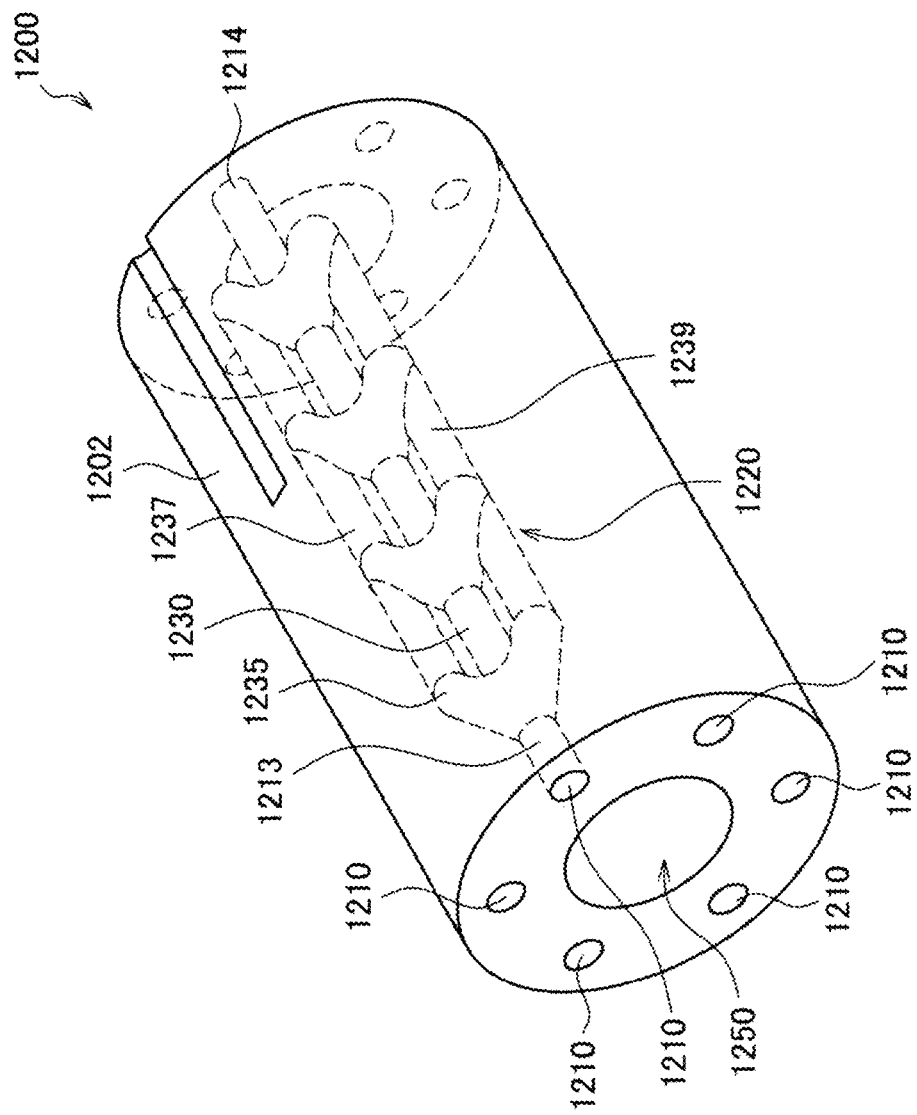
FIG. 16 is a perspective view of a perfume cartridge according to a second modification.

FIG. 12 to FIG. 15 are explanatory diagrams illustrating a perfume cartridge 1100 according to a first modification. FIG. 12 is a perspective view of the perfume cartridge 1100, and illustrates one of six air flow channels 110 in a main body 1102 in a translucent manner. In addition, FIG. 14 is a side view of the perfume cartridge 1100 seen from the radial direction, and FIG. 15 is a front view of the perfume cartridge 1100 seen from the axial direction. In addition, FIG. 16 is a schematic diagram illustrating the configuration of the air flow channel 1110 in an understandable way.

The perfume cartridge 1100 includes the main body 1102, the axial direction hole 1150, and the plurality of air flow channels 1110. The axial direction hole 1150 is centered on the shaft center of the main body 1102. The perfume cartridge 1100 according to the first modification includes the six air flow channels 1110. However, the number of the air flow channels 1110 may be one, four or less, or seven or more. Each of the air flow channels 1110 of the perfume cartridge 1100 according to the first modification has the retainer space 1120, and a first opening 1113 and second opening 1114 that connect the retainer space 1120 with an outside of the main body 1102.

In each of the air flow channels 1110, the first opening 1113 and the second opening 1114 open on respective end faces of the main body 1102 in the axial direction. In addition, each of the retainer spaces 1120 has a main flow channel 1130 and a plurality of containers 1135. The main flow channel 1130 serves as a first segment region formed in the axial direction of the perfume cartridge 1100, and the plurality of containers 1135 serve as a second segment region connected with the main flow channel 1130 at a plurality of positions. For example, the main flow channel 1130 may have an internal diameter of 500 to 3000 μm.

A planar shape of each of the containers 1135 is an arrowhead shape when the container 1135 is seen from the radial direction of the perfume cartridge 1100. In addition, a planar shape of each of the containers 1135 is substantially an oval shape when the container 1135 is seen from the axial direction of the perfume cartridge 1100. In the example illustrated in FIG. 14, the oval shape of the container 1135 is a shape in which a ratio of a length of a major axis to a length of a minor axis is relatively large. In addition, cross-sectional shapes of the container 1135 on the both end sides are circular shapes in the axial direction of the perfume cartridge 1100 (see FIG. 15). Note that, the shape of the container 1135 is not limited to the above described example. In addition, in the illustrated example, each of the air flow channels 1110 has four containers 1135. However, the number of the containers 1135 is not specifically limited. In addition, the intervals between the plurality of containers 1135 in the axial direction may be even or uneven.

This retainer space 1120 has a small pressure drop when air flows in the main flow channel 1130. The air supplied into the air flow channel 110 mainly flows in the main flow channel. On the other hand, each of the containers 1135 is a closed space except for a connection part with the main flow channel 1130. Therefore, it is difficult for air to pass through the containers 1135. When air flows in the main flow channel 1130, the wet perfumes attached to the internal surfaces of the containers 1135 are evaporated little by little, and evaporated aroma components are carried by the air and output to the outside via the second opening 1114. To make it easy for a part of the air flowing in the main flow channel 1130 to enter the containers 1135, the connection parts between the main flow channel 1130 and the containers 1135 may have large areas.

Except for the configuration described above, the perfume cartridge 1100 according to the first modification is similar to the perfume cartridge 200 according to the above-described embodiment.

The perfume cartridge 1100 according to the first modification has the containers 1135 in addition to the main flow channel 1130 in the retainer space 1120 of the air flow channel 1110. Air mainly passes through the main flow channel 1130, and the container 1130 is capable of retaining the wet perfume on its internal surface. Therefore, it is possible to increase amounts of the wet perfumes retained in the air flow channels 1110. This can extend duration of use of the perfume cartridge 1100. In addition, it is possible to further increase the amounts of perfumes retained in the air flow channels 110 in the perfume cartridge 1100 according to the first modification, in the case where surface increase parts are provided in at least the main flow channel 1130 or the containers 1135.

In addition, internal diameters of the main flow channel 1130, the first opening 1113, and the second opening 114 in the perfume cartridge 1100 according to the first modification are set so as not to dramatically reduce pressure drops of air flowing in the air flow channels 1110. Therefore, it is possible to ensure an amount of flow of air including an aroma component in high concentration, thereby outputting the aroma efficiently.

3-2. Second Modification

Figure 17:
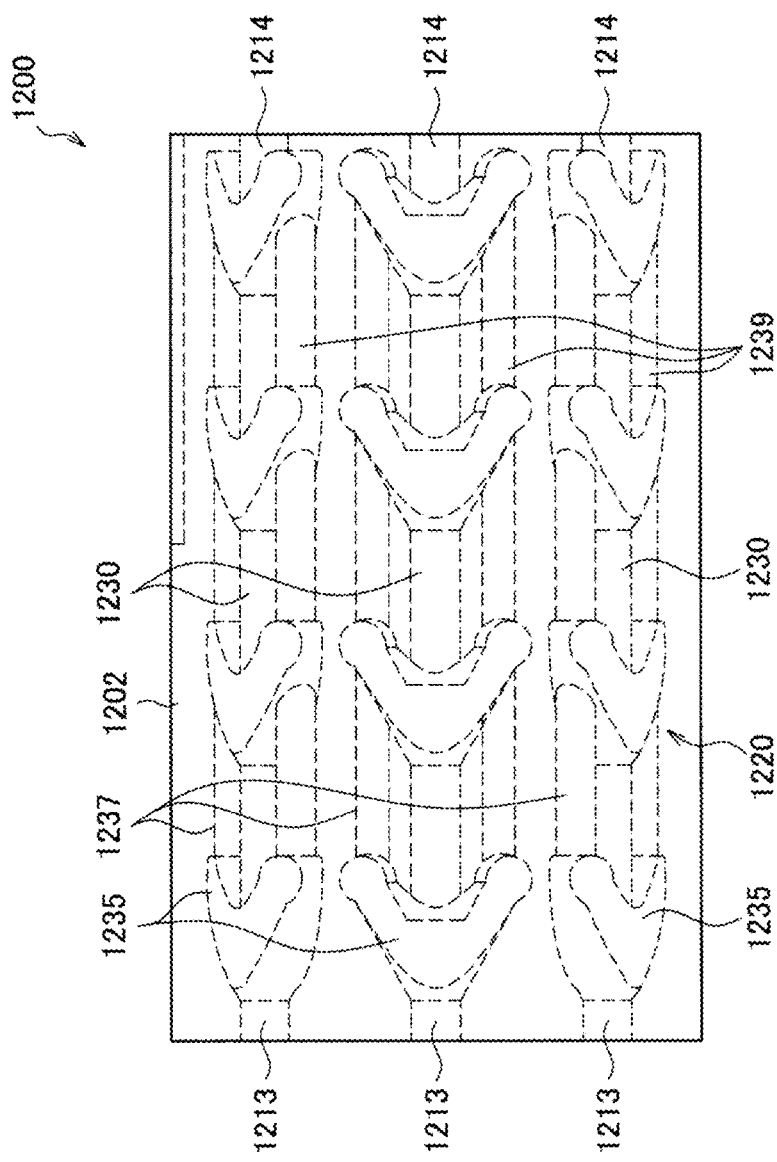
FIG. 17 is a side view of the perfume cartridge according to the second modification seen from the radial direction.
Figure 18:
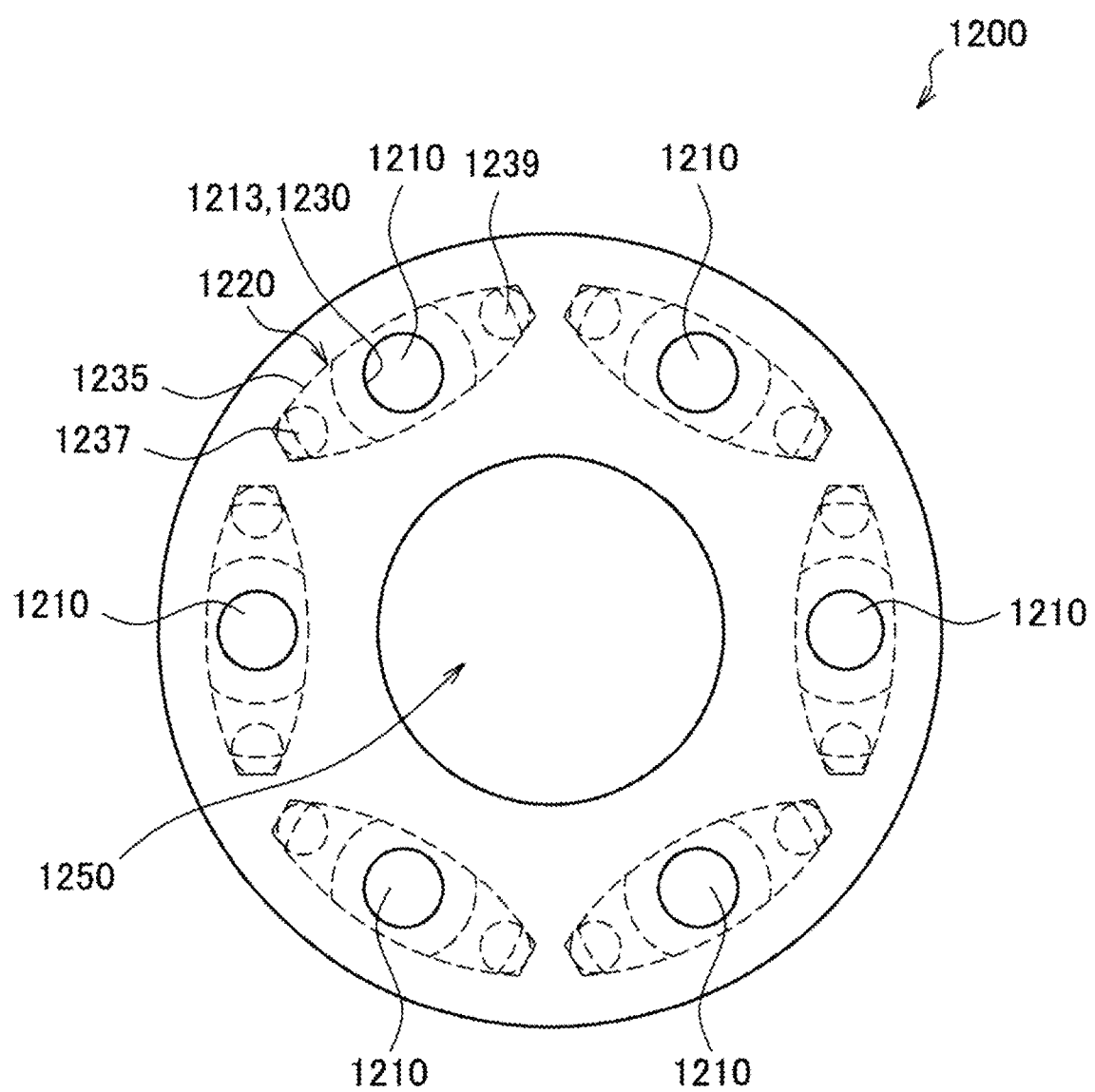
FIG. 18 is a side view of the perfume cartridge according to the second modification seen from the axial direction.
Figure 19:
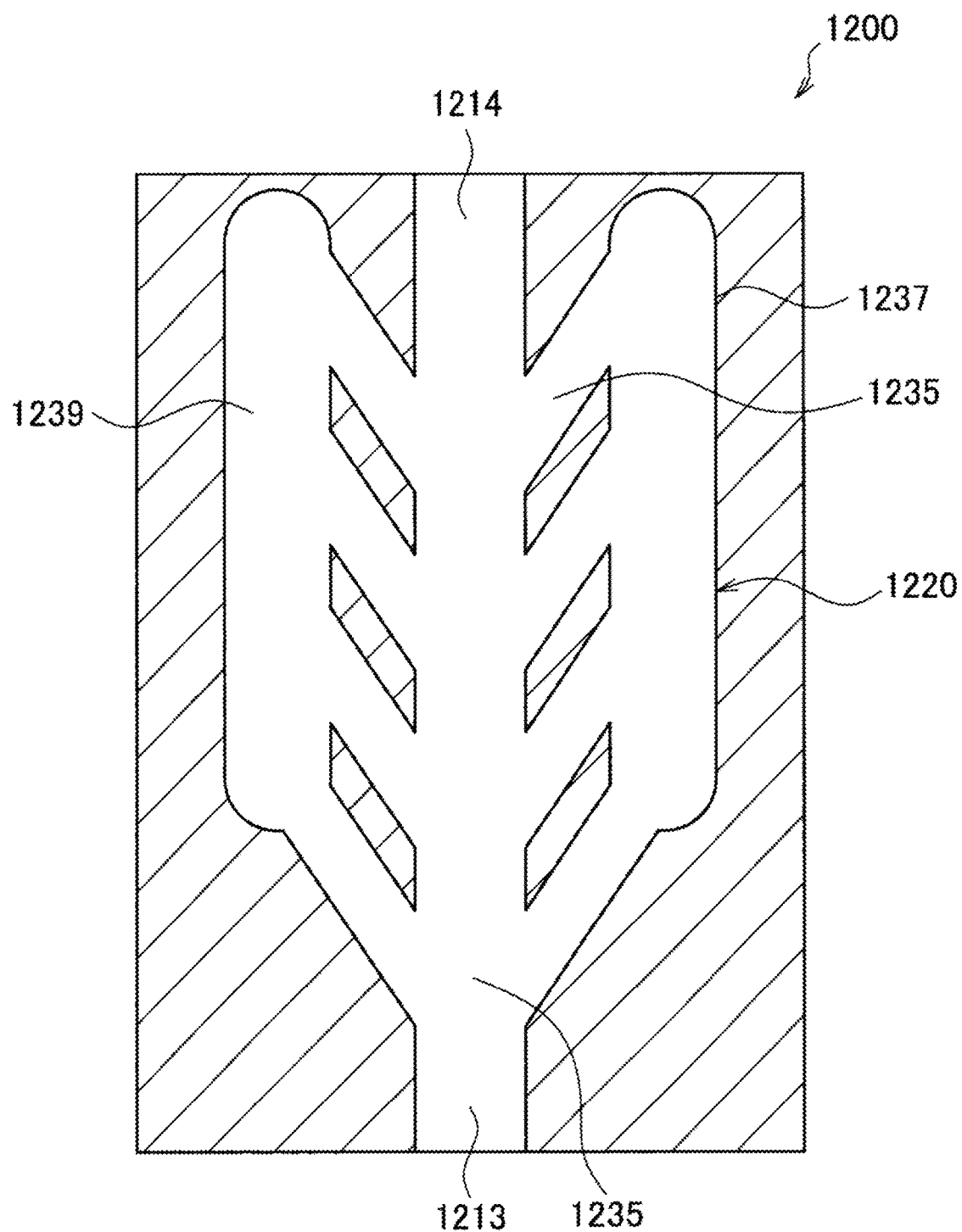
FIG. 19 is a schematic diagram illustrating a configuration of an air flow channel of the perfume cartridge according to the second modification.

FIG. 16 to FIG. 19 are explanatory diagrams illustrating a perfume cartridge 1200 according to a second modification. FIG. 16 is a perspective view of the perfume cartridge 1200, and illustrates one of six air flow channels 1210 in a main body 1202 in a translucent manner. In addition, FIG. 17 is a side view of the perfume cartridge 1200 seen from the radial direction, and FIG. 18 is a front view of the perfume cartridge 1200 seen from the axial direction. In addition, FIG. 19 is a schematic diagram illustrating the configuration of the air flow channel 1210 in an understandable way.

The perfume cartridge 1200 includes the main body 1202, the axial direction hole 1250, and the plurality of air flow channels 1210. The axial direction hole 1150 is centered on the shaft center of the main body 1202. The perfume cartridge 1200 according to the second modification includes the six air flow channels 1210. However, the number of the air flow channels 1210 may be one, four or less, or seven or more. Each of the air flow channels 1210 has the retainer space 1220, and a first opening 1213 and second opening 1214 that connect the retainer space 1220 with an outside of the main body 1202.

The retainer space 1220 of each air flow channel 1210 in the perfume cartridge 1200 according to the second modification includes a main flow channel 1230 serving as the first segment region and a plurality of containers 1235 serving as the second segment region. The main flow channel 1230 may be similar to the retainer space 1120 of the perfume cartridge 1100 according to the first modification. In the second modification, the both ends of the plurality of containers 1235 are connected via a first connection flow channel 1137 serving as the third segment region and a second connection flow channel 1139 serving as the fourth segment region.

In other words, all of one ends among the both ends of the containers 1135 communicates with the first communication flow channel 1237 extending in the axial direction of the perfume cartridge 1120, and all of the other ends communicate with the second connection flow channel 1239 extending in the axial direction of the perfume cartridge 1200. Therefore, the perfume cartridge 1200 according to the second modification is capable of retaining wet perfumes also on internal surfaces of the first communication flow channel 1237 and the second communication flow channel 1239, and it may be possible to further increase amounts of the perfumes to be retained.

In addition, the perfume cartridge 1200 according to the second modification is capable of flowing air between the main flow channel 1230 and the first connection flow channel 1237 or the second connection flow channel 1239, via the containers 1235. This can increase concentration of the aroma component in the air output from the second opening 1214. In addition, the perfume cartridge 1200 according to the second modification is capable of increasing an amount of air flowing in the air flow channels 1210 in comparison with the perfume cartridge 1100 according to the first modification. Therefore, it is possible to output aroma more efficiently.

3-3. Third Modification

Figure 20:
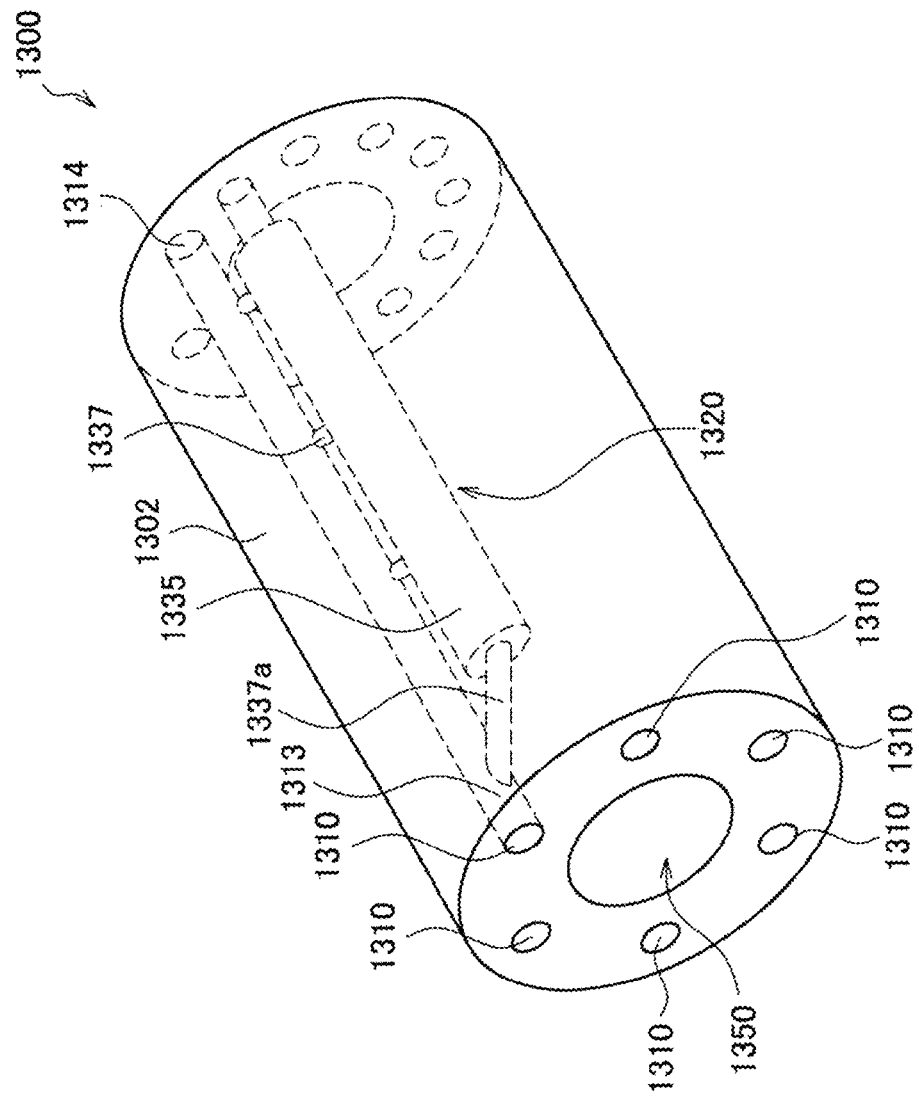
FIG. 20 is a perspective view of a perfume cartridge according to a third modification.
Figure 21:
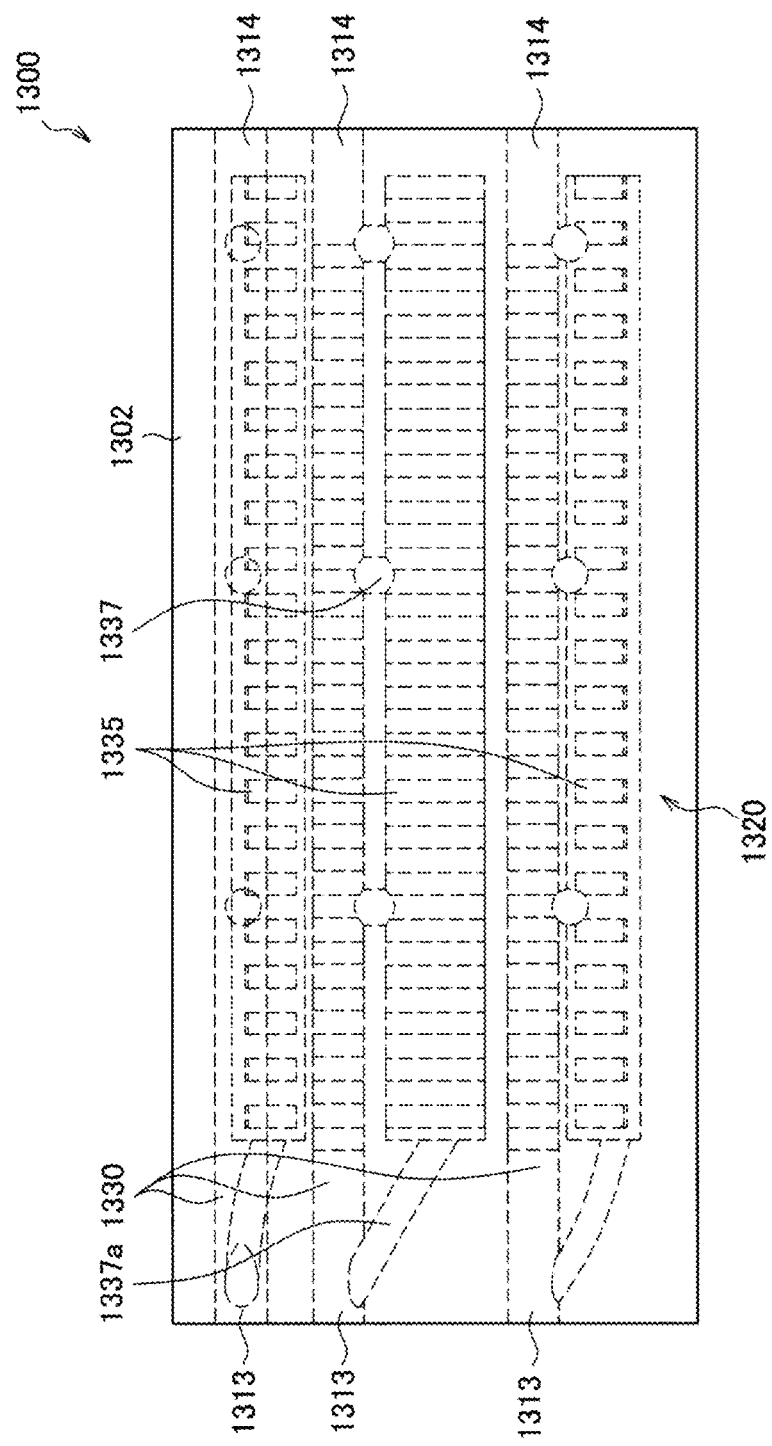
FIG. 21 is a side view of the perfume cartridge according to the third modification seen from the radial direction.
Figure 22:
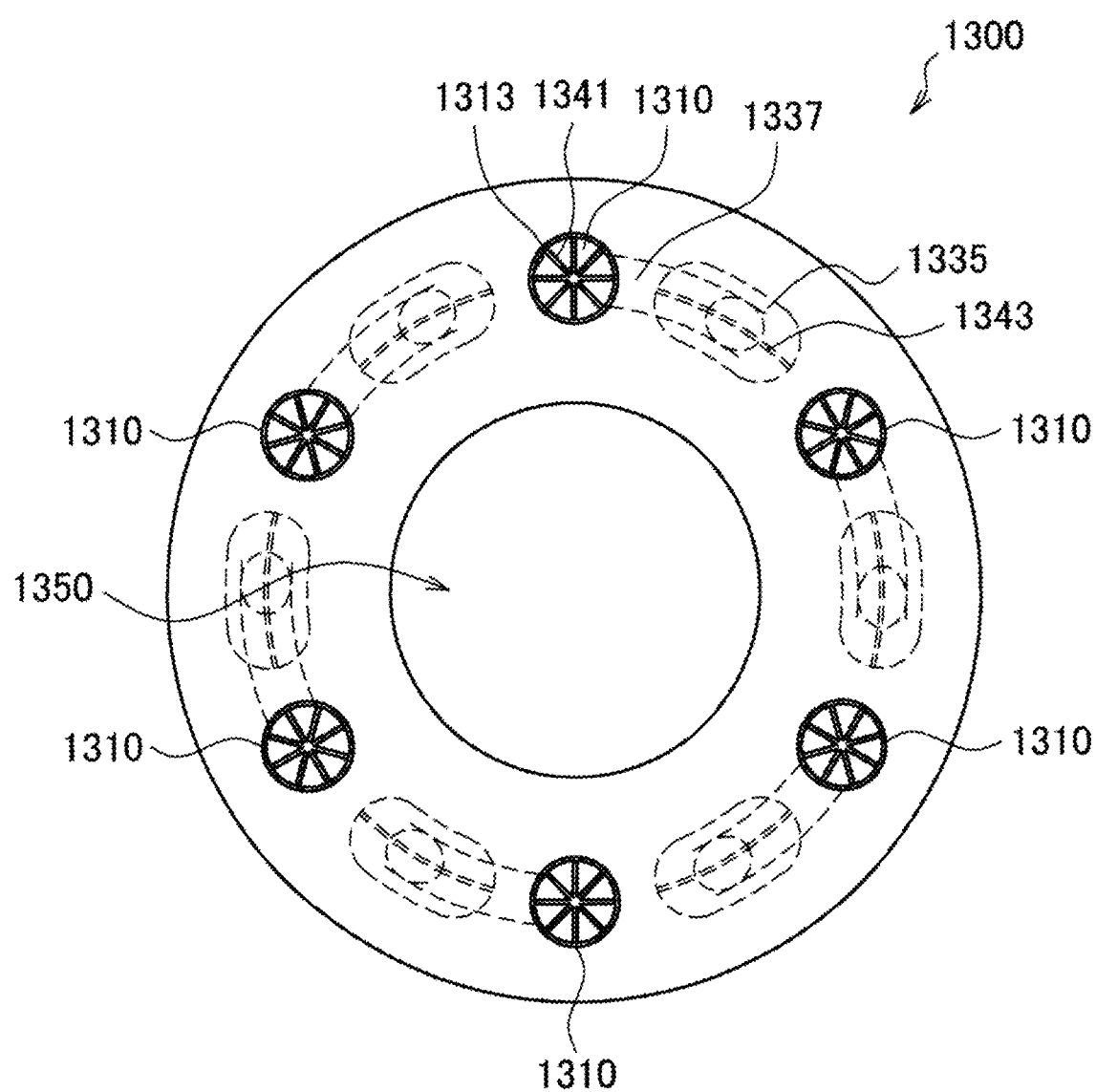
FIG. 22 is a side view of the perfume cartridge according to the third modification seen from the axial direction.
Figure 23:
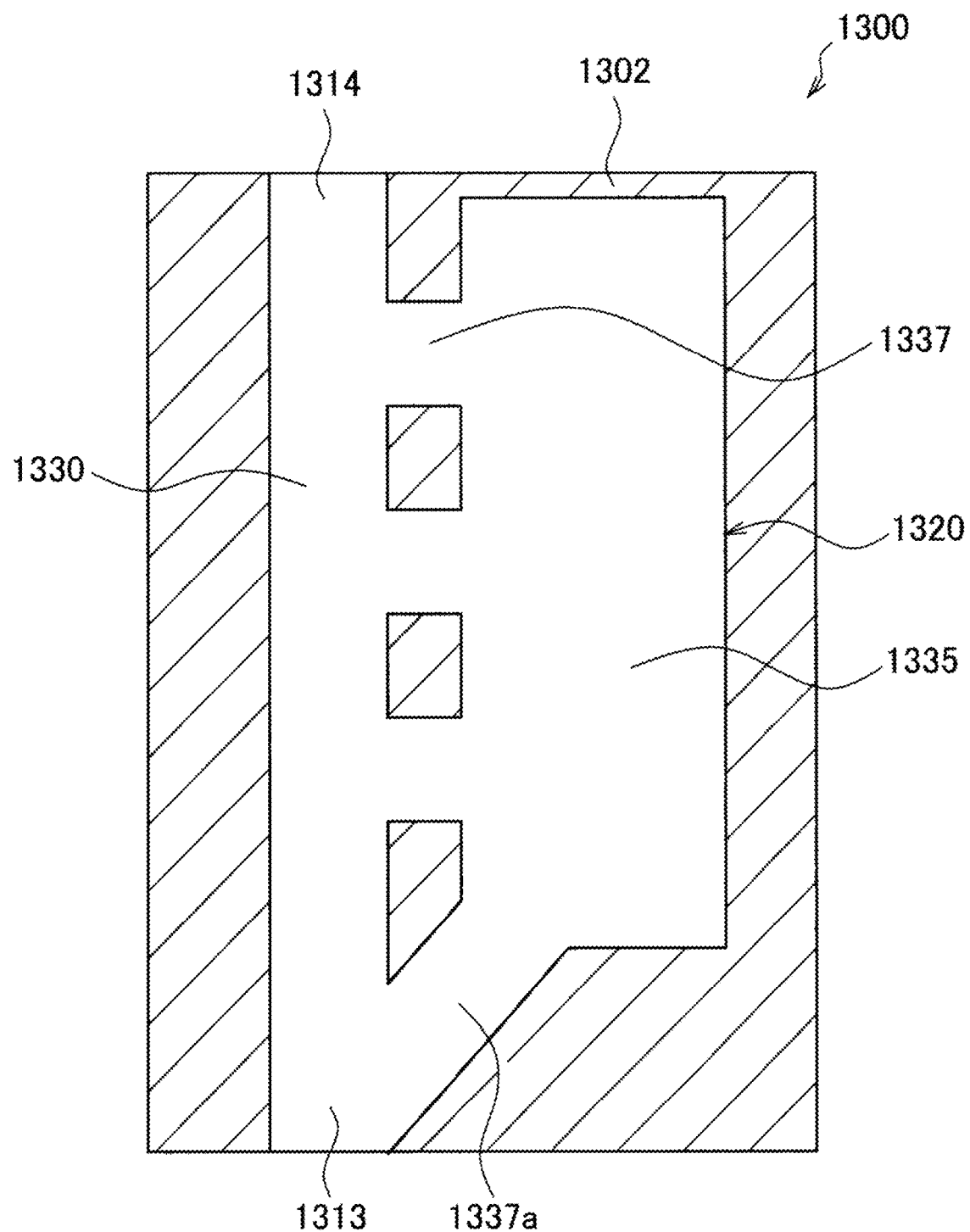
FIG. 23 is a schematic diagram illustrating a configuration of an air flow channel of the perfume cartridge according to the third modification.
Figure 24:
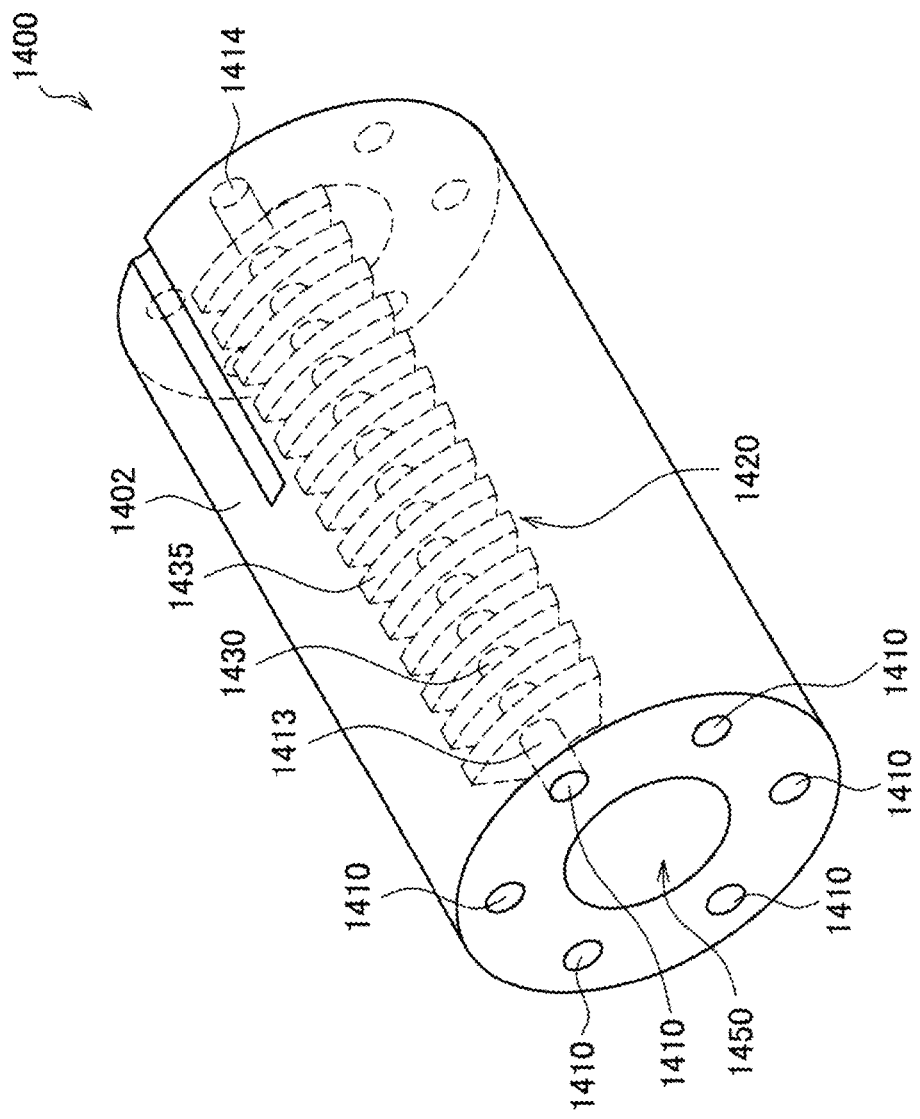
FIG. 24 is a perspective view of a perfume cartridge according to a fourth modification.

FIG. 20 to FIG. 23 are explanatory diagrams illustrating a perfume cartridge 1300 according to a third modification. FIG. 20 is a perspective view of the perfume cartridge 1300, and illustrates one of six air flow channels 1310 in a main body 1302 in a translucent manner. In addition, FIG. 22 is a side view of the perfume cartridge 1300 seen from the radial direction, and FIG. 23 is a front view of the perfume cartridge 1300 seen from the axial direction. In addition, FIG. 24 is a schematic diagram illustrating the configuration of the air flow channel 1310 in an understandable way.

The perfume cartridge 1300 includes the main body 1302, an axial direction hole 1350, and a plurality of air flow channels 1310. The axial direction hole 1350 is centered on the shaft center of the main body 1302. The perfume cartridge 1300 according to the third modification includes the six air flow channels 1310. However, the number of the air flow channels 1310 may be one, four or less, or seven or more. Each of the air flow channels 1310 of the perfume cartridge 1300 according to the third modification has the retainer space 1320, and a first opening 1313 and second opening 1314 that connect the retainer space 1320 with an outside of the main body 1302.

In each of the air flow channels 1310, the first opening 1313 and the second opening 1314 open on respective end faces of the main body 1302 in the axial direction. In addition, each of the retainer spaces 1320 has a main flow channel 1330 and a plurality of containers 1335. The main flow channel 1330 serves as a first segment region formed in the axial direction of the perfume cartridge 1300, and the container 1335 serve as a second segment region connected with the main flow channel 1130 at a plurality of positions. For example, the main flow channel 1330 may have an internal diameter of 500 to 3000 µm. The main flow channel 1330 includes a cross-shaped surface increase part 1341 in which eight unit radii are arranged at regular intervals of 45°. It is possible to arrange a plurality of the cross-shaped surface increase parts 1341 in the axial direction of the main flow channel 1330.

The container 1335 has a larger cross-sectional area in the circumferential direction of the perfume cartridge 1300 in comparison with a cross-sectional area of the main flow channel 1330. For example, the cross section of the container 1335 may have an oval shape in which a major axis curves along the circumferential direction of the main body 1302. In this case, the length of the cross section having the oval shape in a minor axis direction may be 50 to 3000 µm, and the length in a major axis direction may be 100 to 6000 µm. In addition, the container 1335 includes a plate-shaped surface increase part 1343 on the major axis of the cross section having the oval shape. The plate-shaped surface increase part 1343 has a predetermined thickness in the radial direction of the perfume cartridge 1300, and formed along the axial direction of the perfume cartridge 1300. The length of the plate-shaped surface increase part 1343 in the axial direction may be set appropriately. For example, a plurality of the plate-shaped surface increase parts 1343 having the length of 5 to 3000 µm may be arranged at intervals of 5 to 3000 µm.

The container 1335 communicates with the main flow channel 1330 via a plurality of communication channels 1337, but does not open to an outside of the main body 1302 without the first opening 1313 and the second opening 1314. For example, each of the communication channels 1337 may have an internal diameter of 50 to 3000 µm. In addition, in the illustrated example, each of the air flow channels 1310 has four communication channels 1337. However, the number of the communication channels 1337 is not specifically limited. In addition, the intervals between the plurality of communication channels 1337 in the axial direction may be even or uneven.

In the retainer space 1320, the main flow channel 1330 and the container 1335 have different cross-sectional areas. Therefore, a pressure drop obtained when air flows in the main flow channel 1330 is different from a pressure drop obtained when air flows in the container 1335. With regard to the plurality of communication channels 1337, a communication channel 1337a closest to the first opening 1313 tilts from the main flow channel 1330 to the container 1335. This enables air supplied into the air flow channel 1310 via the first opening 1313 to easily enter the container 1335.

Except for the configuration described above, the perfume cartridge 1300 according to the third modification is similar to the perfume cartridge 200 according to the above-described embodiment.

The retainer space 1320 of each air flow channel 1310 in the perfume cartridge 1300 according to the third modification also includes the container 1335 and the plurality of communication channels 1337 in addition to the main flow channel 1330. Air mainly passes through the main flow channel 1130, the container 1335 is capable of retaining the wet perfume on its internal surface, and the plurality of communication channels 1337 connect the main flow channel 1330 with the container 1335. Therefore, it is possible to increase amounts of the wet perfumes retained in the air flow channels 1310. This can extend duration of use of the perfume cartridge 1300. In addition, it is also possible to further increase the amounts of perfumes retained in the air flow channels 1310 in the perfume cartridge 1300 according to the third modification, in the case where the cross-shaped surface increase part 1341 or the plate-shaped surface increase part 1343 are provided in the main flow channel 1330 or the container 1335.

In addition, the perfume cartridge 1300 according to the second modification is capable of flowing air between the main flow channel 1330 and the container 1335 via the container 1335. This can increase concentration of the aroma component in the air output from the second opening 1314. In addition, internal diameters of the main flow channel 1330, the first opening 1313, and the second opening 1314 in the perfume cartridge 1300 according to the third modification are set so as not to dramatically reduce pressure drops of air flowing in the air flow channels 1310. Therefore, it is possible to ensure an amount of flow of air including an aroma component in high concentration, thereby outputting the aroma efficiently.

3-4. Fourth Modification

Figure 25:
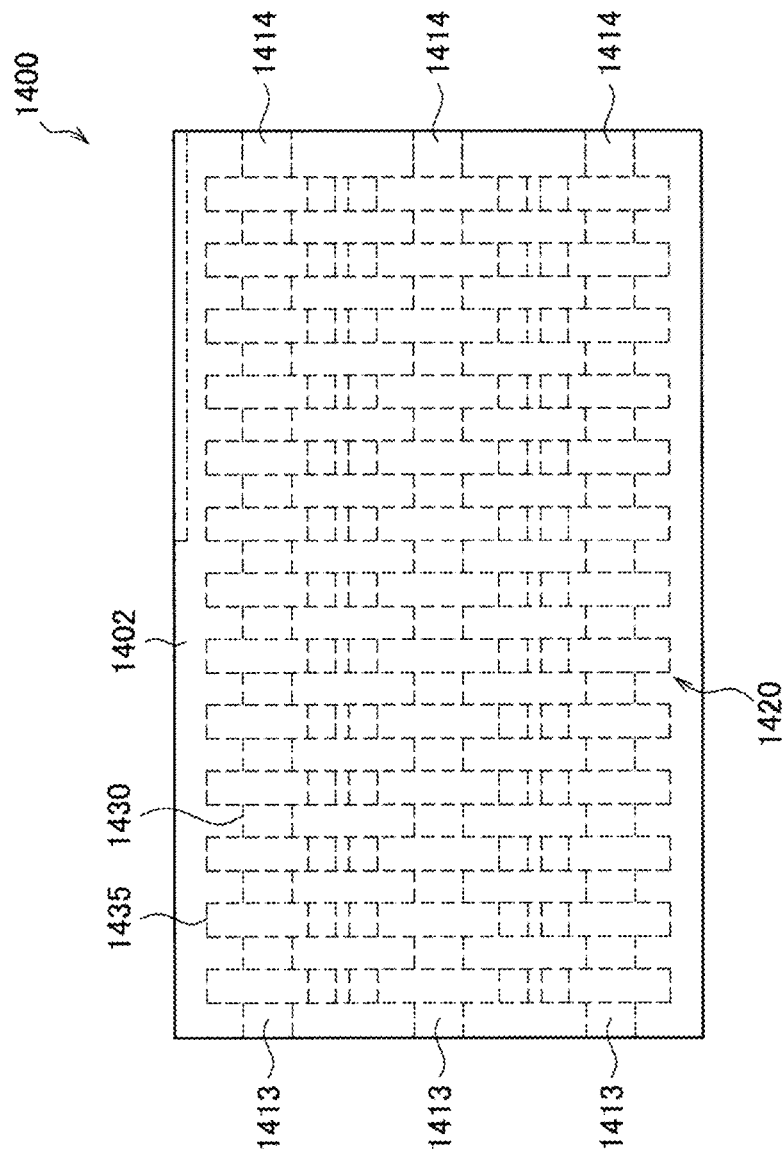
FIG. 25 is a side view of the perfume cartridge according to the fourth modification seen from the radial direction.
Figure 26:
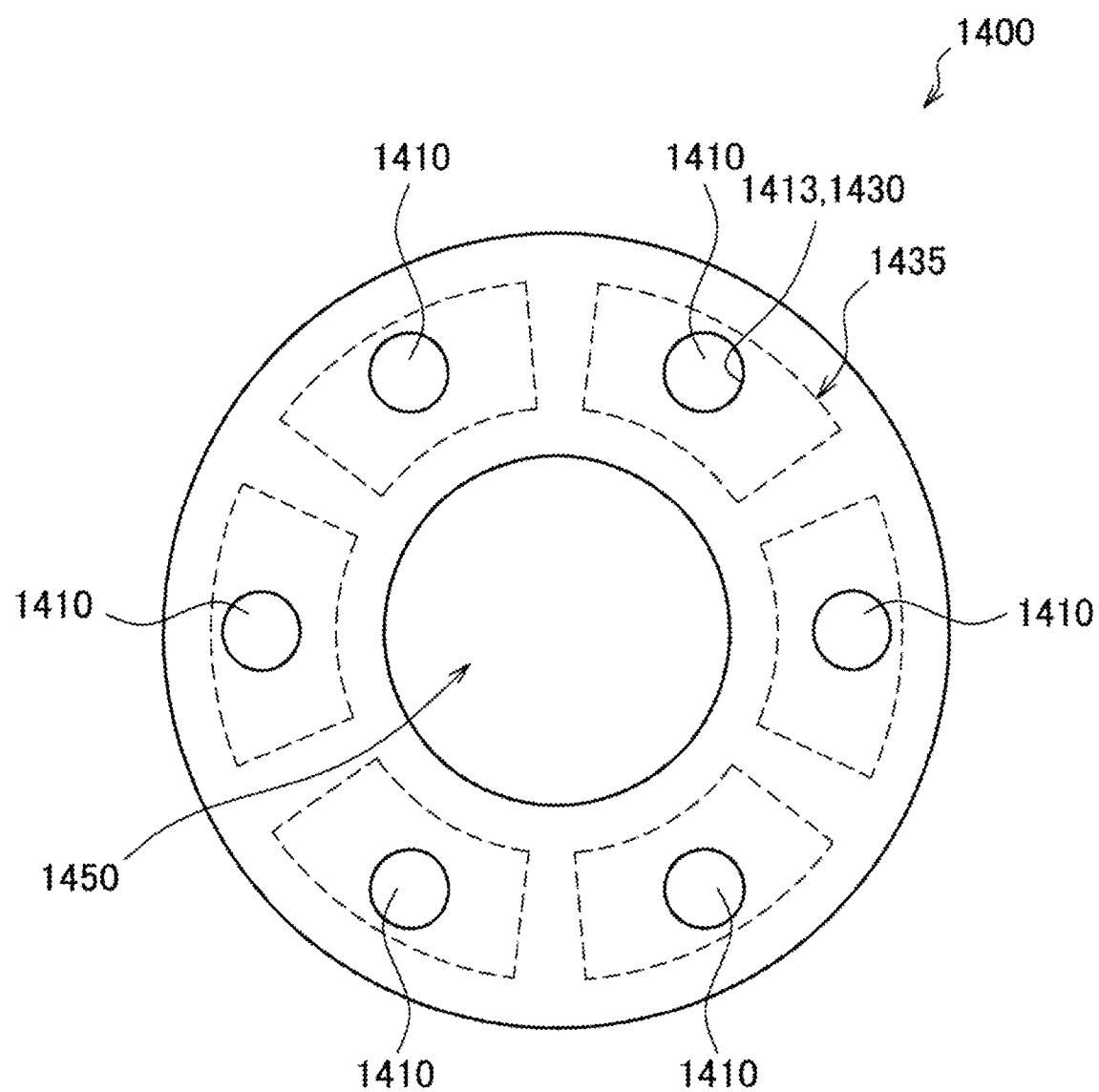
FIG. 26 is a side view of the perfume cartridge according to the fourth modification seen from the axial direction.
Figure 27:
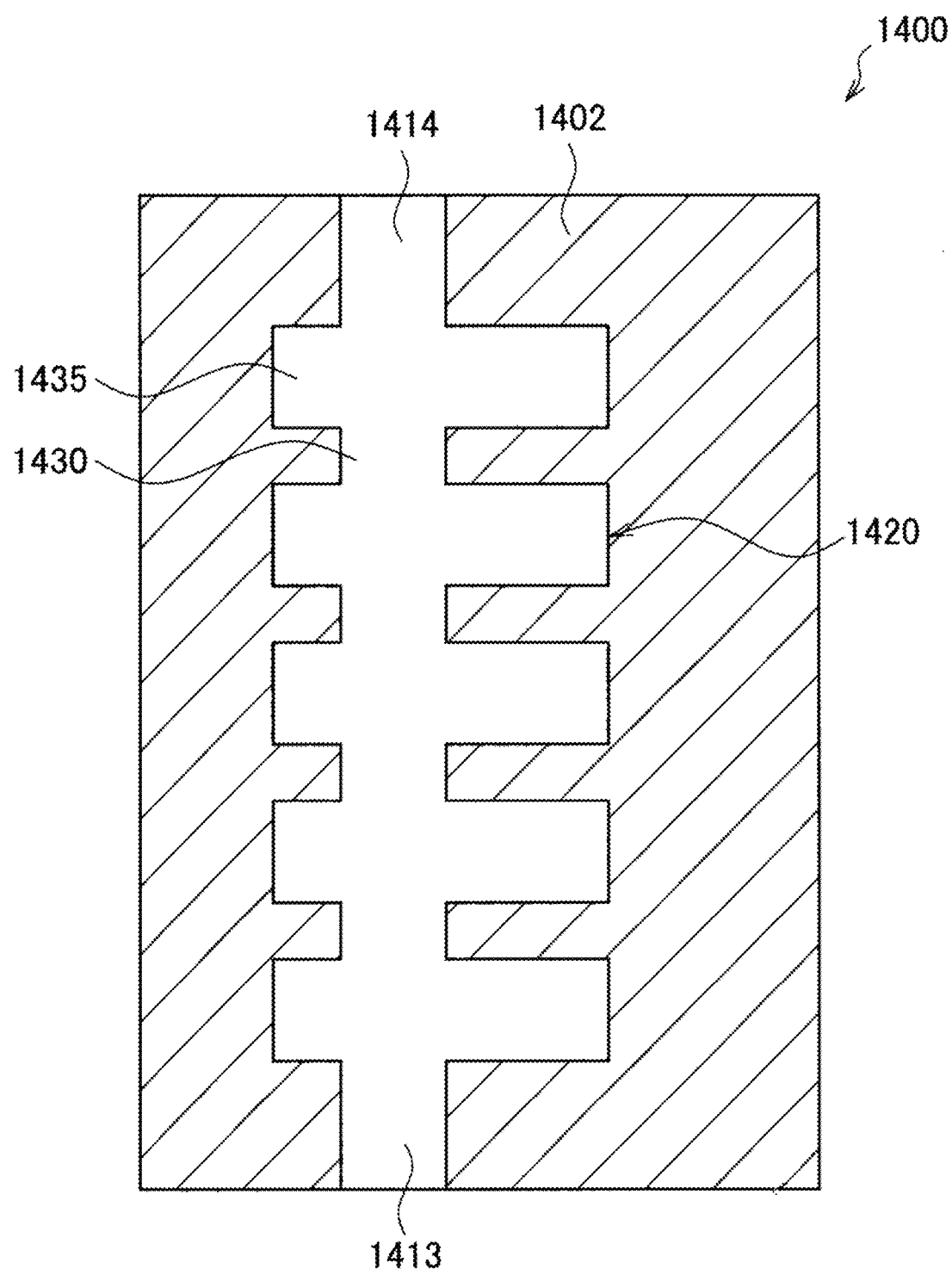
FIG. 27 is a schematic diagram illustrating a configuration of an air flow channel of the perfume cartridge according to the fourth modification.

FIG. 24 to FIG. 27 are explanatory diagrams illustrating a perfume cartridge 1400 according to a fourth modification. FIG. 24 is a perspective view of the perfume cartridge 1400, and illustrates one of six air flow channels 1410 in a main body 1402 in a translucent manner. In addition, FIG. 25 is a side view of the perfume cartridge 1400 seen from the radial direction, and FIG. 26 is a front view of the perfume cartridge 1400 seen from the axial direction. In addition, FIG. 27 is a schematic diagram illustrating the configuration of the air flow channel 1410 in an understandable way.

The perfume cartridge 1400 includes the main body 1402, an axial direction hole 1450, and a plurality of air flow channels 1410. The axial direction hole 1150 is centered on the shaft center of the main body 1402. The perfume cartridge 1400 according to the fourth modification includes the six air flow channels 1410. However, the number of the air flow channels 1410 may be one, four or less, or six or more. Each of the air flow channels 1410 of the perfume cartridge 1400 according to the fourth modification has a retainer space 1420, and a first opening 1413 and second opening 1414 that connect the retainer space 1420 with an outside of the main body 1402.

In each of the air flow channels 1410, the first opening 1413 and the second opening 1414 open on respective end faces of the main body 1402 in the axial direction. In addition, each of the retainer spaces 1420 has a main flow channel 1430 and containers 1435. The main flow channel 1430 serves as a first segment region formed in the axial direction of the perfume cartridge 1400, and the container 1435 serve as a second segment region connected with the main flow channel 1130 at a plurality of positions. For example, the main flow channel 1430 may have an internal diameter of 500 to 3000 µm.

The container 1435 has a larger cross-sectional area in the circumferential direction of the perfume cartridge 1400 in comparison with a cross-sectional area of the main flow channel 1430. For example, a cross-sectional shape of each of the containers 1435 in the circumferential direction of the perfume cartridge 1400 may be an approximate trapezoidal shape. In addition, for example, each of the containers 1435 (length in the axial direction of the perfume cartridge 1400) may have a thickness of 10 to 5000 µm. The main flow channel 1430 penetrates through the centers of the plurality of containers 1435. The number of the containers 1435 provided in each air flow channel 1410 is not specifically limited. In addition, the intervals between the plurality of containers 1435 in the axial direction may be even or uneven.

This retainer space 1420 has a small pressure drop when air flows in the main flow channel 1430. The air supplied into the air flow channel 1410 mainly flows in the main flow channel. On the other hand, each of the containers 1435 is a closed space except for connection parts with the main flow channel 1430. Therefore, it is difficult for air to pass through the containers 1135. When air flows in the main flow channel 1430, the wet perfumes attached to the internal surfaces of the containers 1435 are evaporated little by little, and evaporated aroma components are carried by the air and output to the outside via the second opening 1414. To make it easy for a part of the air flowing in the main flow channel 1430 to enter the containers 1435, the connection parts between the main flow channel 1430 and the containers 1435 may have large areas.

Except for the configuration described above, the perfume cartridge 1400 according to the fourth modification is similar to the perfume cartridge 200 according to the above-described embodiment.

The perfume cartridge 1400 according to the fourth modification also has the containers 1435 in addition to the main flow channel 1430 in the retainer space 1420 of the air flow channel 1410. Air mainly passes through the main flow channel 1430, and the containers 1435 are capable of retaining the wet perfume on its internal surface. Therefore, it is possible to increase amounts of the wet perfumes retained in the air flow channels 1410. This can extend duration of use of the perfume cartridge 1400. In addition, it is also possible to further increase the amounts of perfumes retained in the air flow channels 1410 in the perfume cartridge 1400 according to the fourth modification, in the case where surface increase parts are provided in at least the main flow channel 1430 or the containers 1435.

In addition, the perfume cartridge 1400 according to the fourth modification is capable of flowing air between the main flow channel 1430 and the containers 1435 via the containers 1435. This can increase concentration of the aroma component in the air output from the second opening 1414. In addition, internal diameters of the main flow channel 1430, the first opening 1413, and the second opening 1414 in the perfume cartridge 1400 according to the fourth modification are set so as not to dramatically reduce pressure drops of air flowing in the air flow channels 1410. Therefore, it is possible to ensure an amount of flow of air including an aroma component in high concentration, thereby outputting the aroma efficiently.

3-5. Fifth Modification

Figure 28:
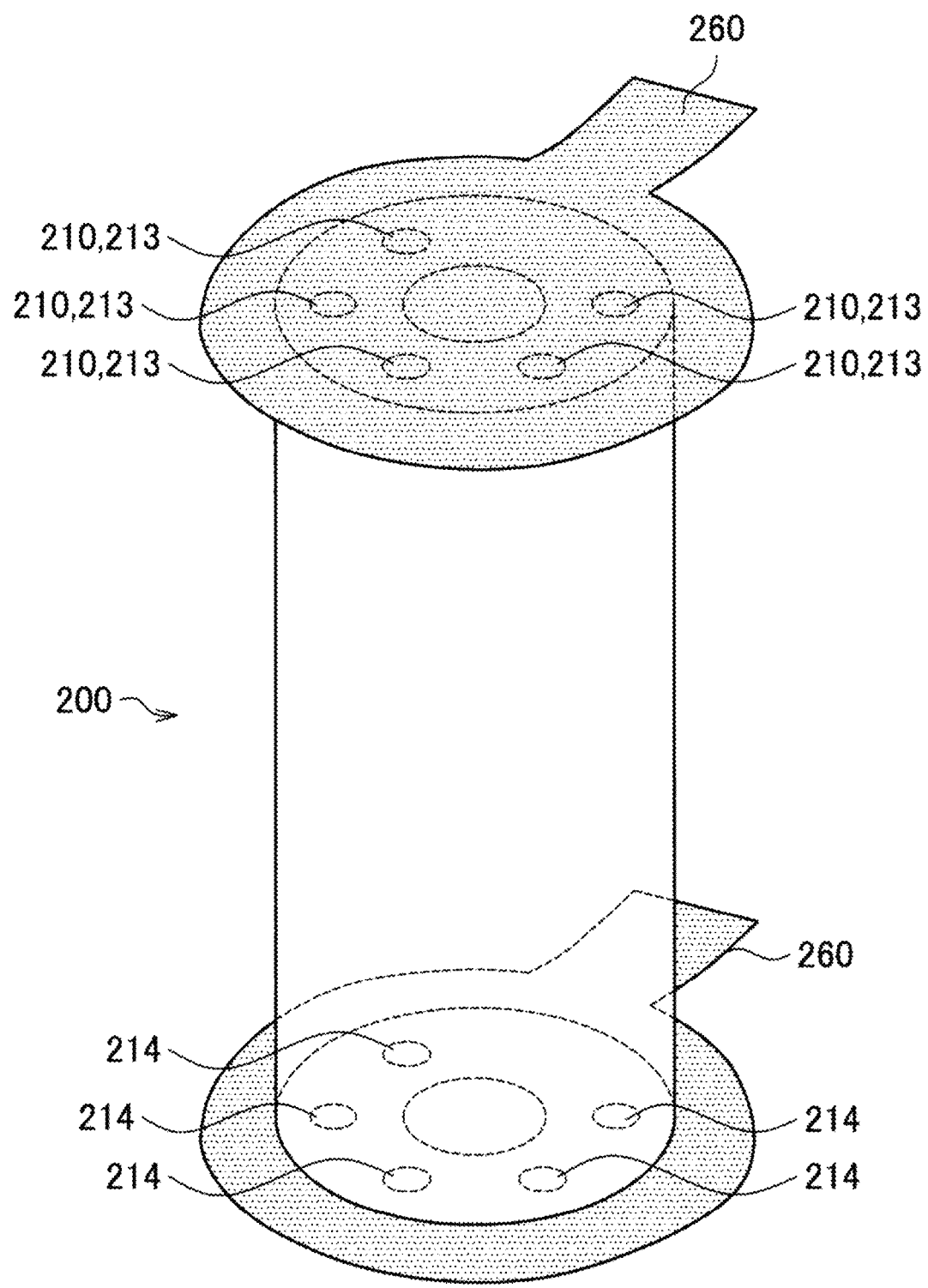
FIG. 28 is a perspective view illustrating an example of a configuration of a perfume cartridge according to a fifth modification.
Figure 29:
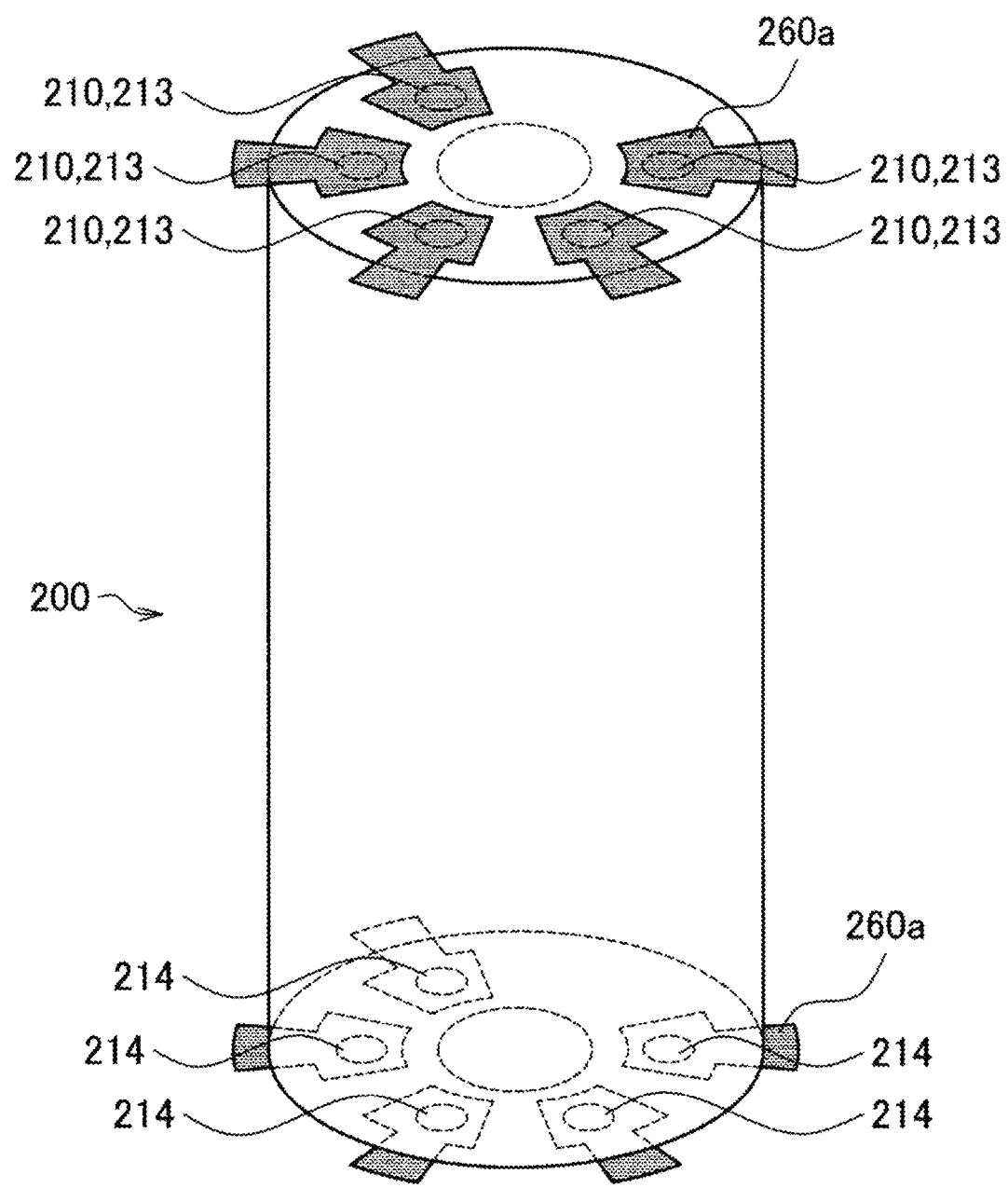
FIG. 29 is a perspective view illustrating another configuration of a seal member.

FIG. 28 and FIG. 29 illustrate an example of the perfume cartridge 200 including seal members 260 that are put on the unused perfume cartridge 200 according to the above described embodiment during the perfume cartridge 200 is stored or shipped. FIG. 28 is an explanatory diagram illustrating an example of the perfume cartridge 200 on which the seal members 260 are put. In the fifth modification, the first openings 213 and the second openings 214 of the air flow channels 210 of the perfume cartridge 200 are sealed by the seal members 260. When using the perfume cartridge 200, the seal members 260 are removed from the perfume cartridge 200. The seal members 260 are capable of preventing outside air from entering into the perfume cartridge 200 during the perfume cartridge 200 is kept unused. Therefore, it is possible to prevent perfumes from getting oxidized.

For example, the seal members 260 may be heat seal films. Alternatively, the seal members 260 may be resin films that are to be attached to the respective end faces of the perfume cartridge 200 by using an adhesive or the like. In addition, each of the seal members 260 may be capable of sealing a part all of the plurality of first openings 213 or the plurality of second openings 214. For example, as illustrated in FIG. 28, it is possible to use a single seal member 260 to seal the plurality of first openings 213 or the plurality of second openings 214.

Alternatively, as illustrated in FIG. 29, it is possible to use separate seal members 260a each of which seals one of the first openings 213 or one of the second openings 214. If the first openings 213 and the second openings 214 are sealed by the separate seal members 260a, it is possible to separately remove the seal members 260a put on the air flow channel 210 corresponding to a perfume that a user wants to use, when using the perfume cartridge 200. Accordingly, it is possible to use the aroma provision device while the seal members 260 are kept attached to unused air flow channels 210. This enables to increase sustainability of the aroma retained in each air flow channel 210.

3-6. Sixth Modification

Figure 30:
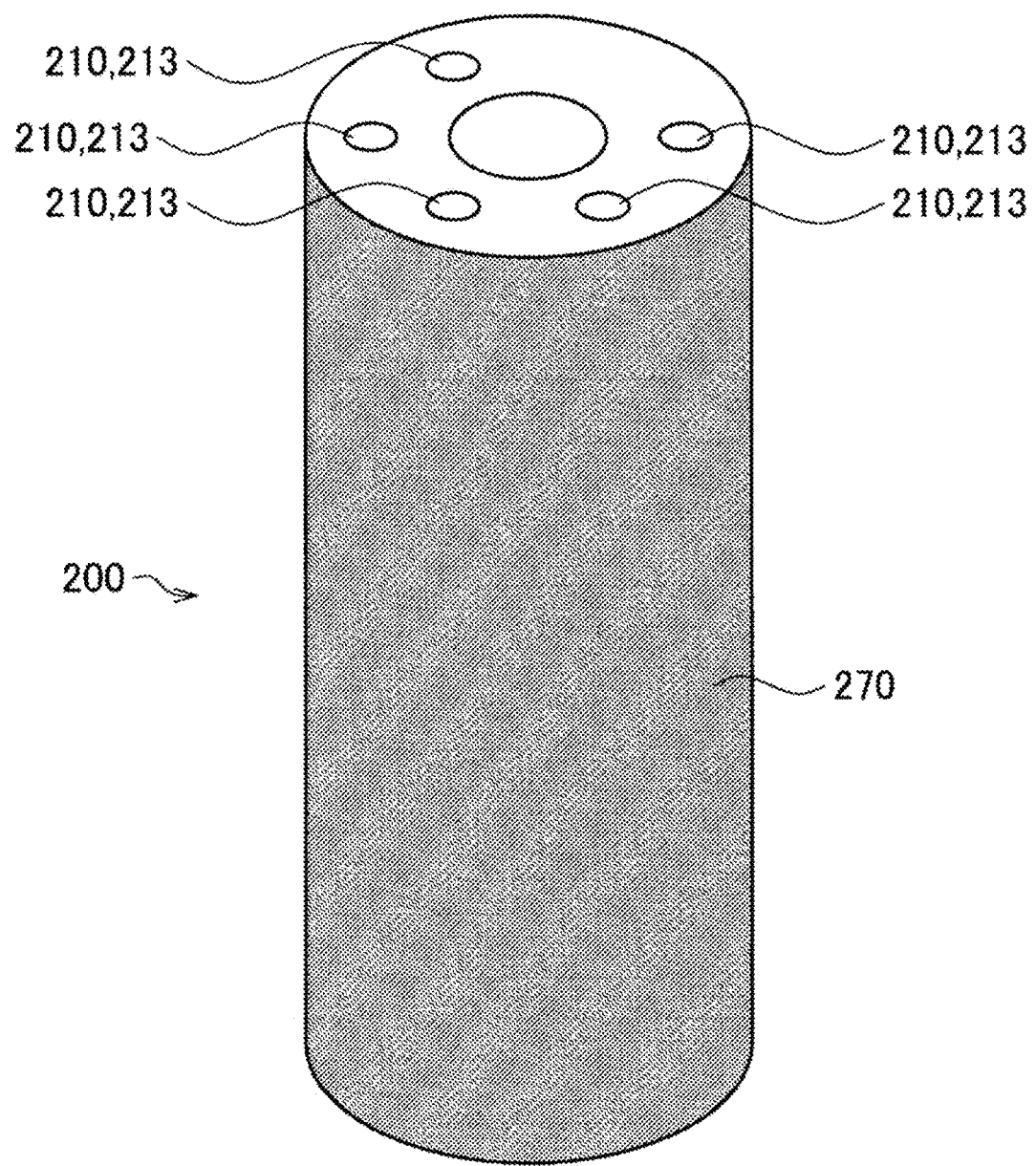
FIG. 30 is a perspective view illustrating an example of a configuration of a perfume cartridge according to a sixth modification.

FIG. 30 illustrates an example of the perfume cartridge 200 provided with a light-blocking member 270 on its outer periphery. FIG. 30 is s an explanatory diagram illustrating an example of a configuration of the perfume cartridge 200 according to a sixth modification. In the sixth modification, the light-blocking member 270 that blocks light covers a part or all of the outer periphery of the perfume cartridge 200. For example, as illustrated in FIG. 30, the light-blocking member 270 covers the entire outer periphery of the perfume cartridge 200 while the perfume cartridge 200 is kept unused. This can prevent perfumes retained in the perfume cartridge 200 from being irradiated with light such as sunlight or illumination light while the perfume cartridge 200 is kept unused. Therefore, it is possible to prevent perfumes from getting oxidized.

3-7. Seventh Modification

Figure 31:
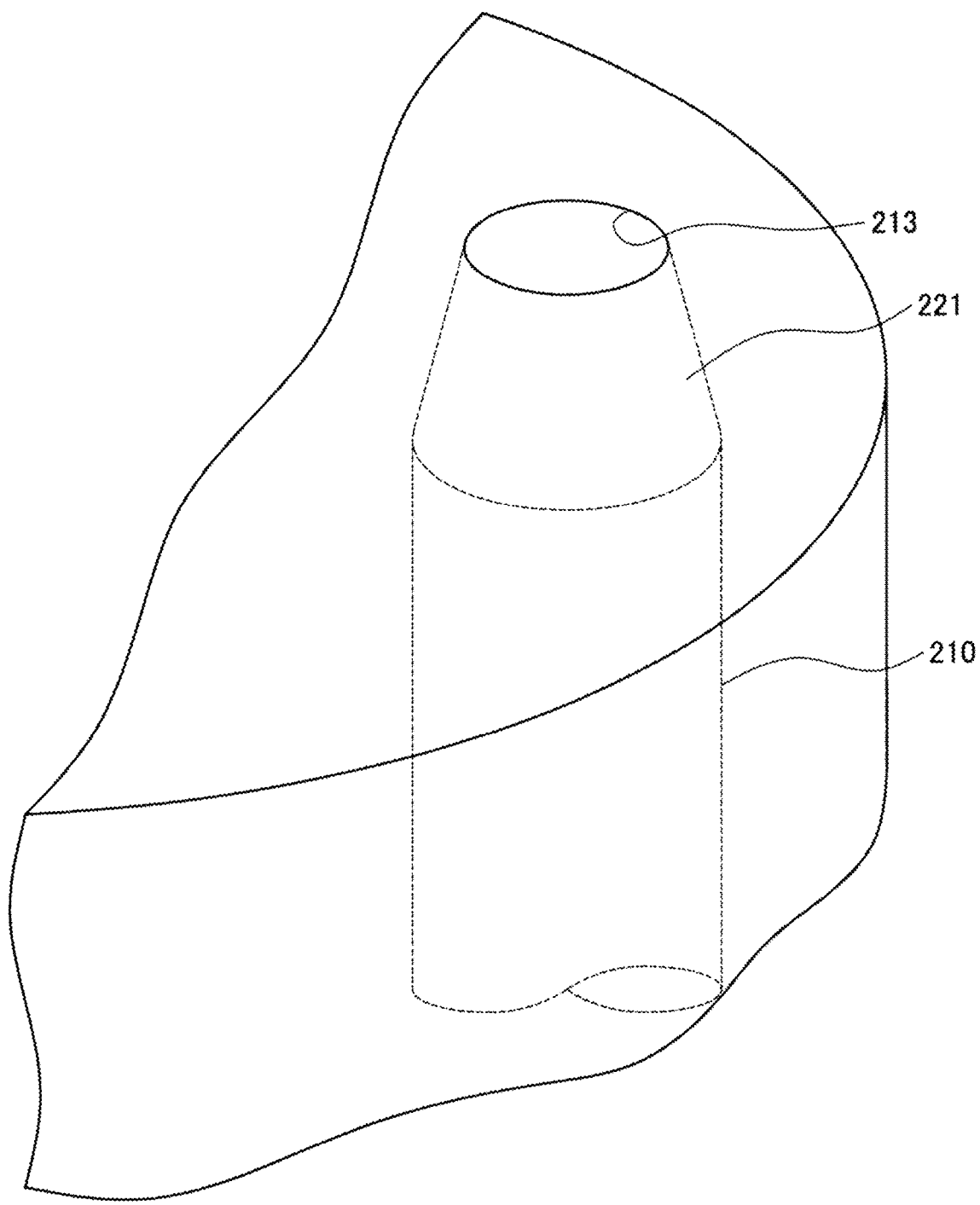
FIG. 31 is a perspective view illustrating an example of a configuration of a perfume cartridge according to a seventh modification.

FIG. 31 is an explanatory diagram illustrating the perfume cartridge 200 according to a seventh modification. In an air flow channel 210 of the perfume cartridge 200 according to the seventh modification, a tapered part 221 is provided on a second opening 214. The tapered part 221 has diameters gradually narrowing towards an opening end. The tapered part 221 provided on the second opening 214 is capable of narrowing down air output via the second opening 214. Therefore, it is possible to suppress diffusion of output air. Accordingly, it is possible to improve straightness of flow of the output air, and it is possible to use the aroma provision device 1 as a device appropriate for personal use.

Note that, a position at which diameters of the tapered part 221 at the second opening 214 start narrowing or a taper angle of the tapered part 221 may be appropriately set in accordance with the size of the second opening 214, pressure of air supplied into the air flow channel 210, or the like. In addition, similar effects can be obtained by providing a tapered part on the aroma output port 112 of the cover 100 that communicates with the second opening 214. The tapered part has diameters gradually narrowing towards a tip.

3-7. Eighth Modification

Figure 32:
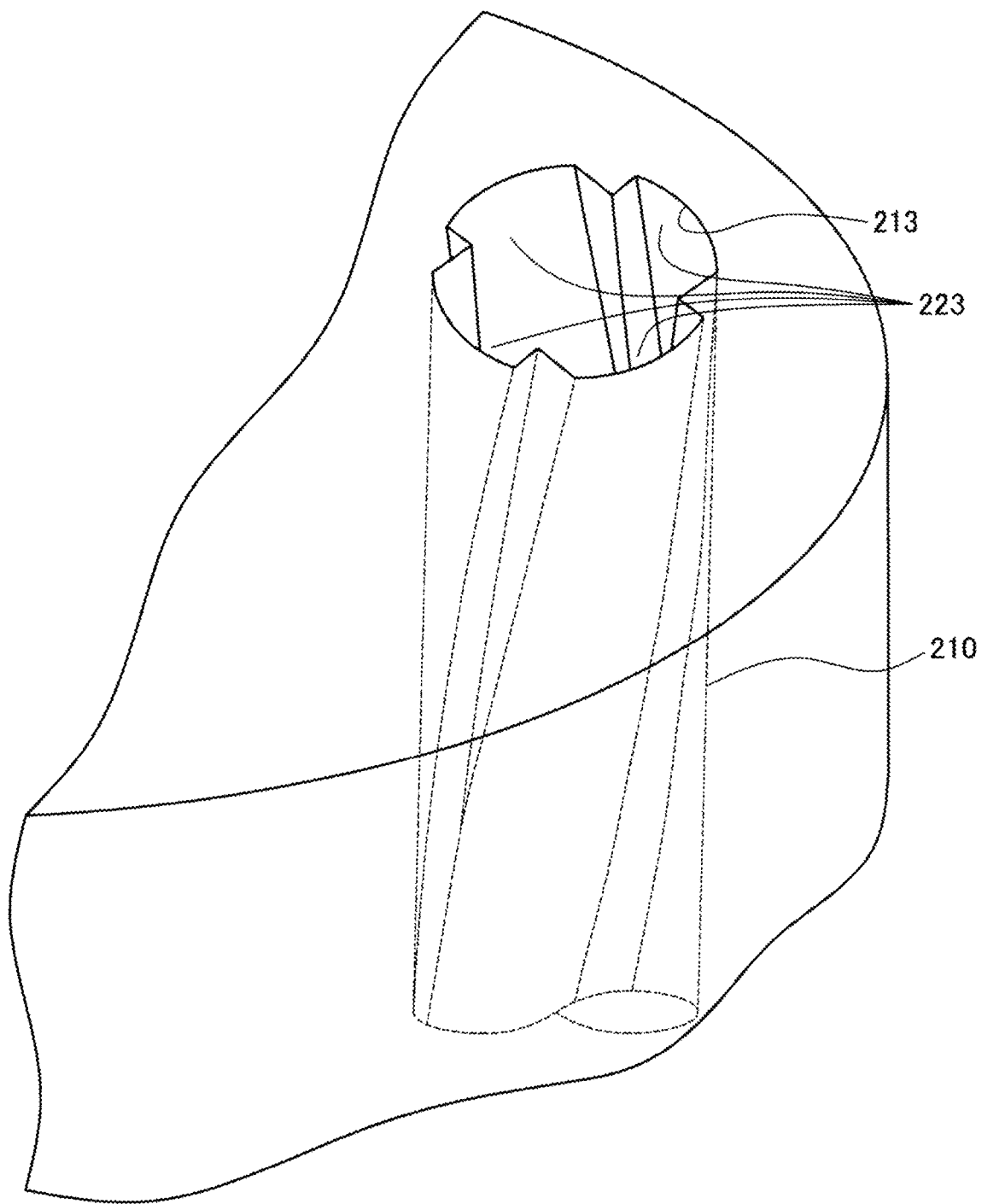
FIG. 32 is a perspective view illustrating an example of a configuration of a perfume cartridge according to an eighth modification.

FIG. 32 is an explanatory diagram illustrating the perfume cartridge 200 according to an eighth modification. In the perfume cartridge 200 according to the eighth modification, spiral grooves 223 are provided on the inner periphery of a second opening 214 of an air flow channel 210. The spiral grooves 223 in the second opening 214 are capable of giving turning ability to air output from the second opening 214, and capable of improving straightness of flow of the output air due to the gyro effect. Therefore, it is possible to improve the straightness of the output air. Note that, the number of the spiral grooves 223 and transverse cross-sectional shapes of the spiral grooves 223 are not limited to the example illustrated in FIG. 32. The number of the spiral grooves 223 may be other numbers, and the spiral grooves 223 may have other transverse cross-sectional shapes.

4. Cover And Retainer Protection Structure

Next, a structure for protecting the cover 100 and the retainer 400 that retain the perfume cartridge 200 will be described. As described above, the aroma provision device 1 according to the embodiment uses the perfume cartridge 200 in which wet perfumes are attached to the inner peripheries of the air flow channels 210. The wet perfumes are essential oils or liquids obtained by diluting the essential oils with ethanol. In the case where the cover 100 or the retainer 200 configured to retain the perfume cartridge 200 include organic polymeric resin compositions, sometimes the cover 100 or the retainer 400 are deteriorated by evaporated perfumes and liquid perfumes leaking from the perfume cartridge 200. In other words, since such organic polymeric resin compositions have poor drug resistance, organic polymeric resin compositions may be subjected to so-called chemical attack, and the deterioration may be occurred by the liquid perfumes or the evaporated perfumes.

On the other hand, when coating films having oil repellency are stacked on at least the inner face of the cover 100 or the retainer 400 or when a structure with oil repellency is provided on at least the inner face of the cover 100 or the retainer 400, it is possible to protect the cover 100 or the retainer 400 from the chemical attack due to the perfumes. It is also possible for the cover 100 or the retainer 400 to include both the coating film having oil repellency and the structure having oil repellency.

In the case where the coating film having oil repellency is stacked on at least one of the cover 100 and the retainer 400, polymeric materials including fluorocarbon polymer may be used as the coating film having oil repellency, for example. Examples of the polymeric materials including fluorocarbon polymer include polytetrafluoroethylene, polychlorotrifluoroethylene, polyvinylidene fluoride, polyvinyl fluoride, perfluoroalkoxy alkane, tetrafluoroethylene-hexafluoropropylene copolymer, ethylene-tetrafluoroethylene copolymer, ethylene-chlorotrifluoroethylene copolymer, and the like. However, the coating film having oil repellency is not limited to the coating film described above.

However, in such a case, sometimes sufficient protection effects from the chemical attack cannot be obtained when the film thickness of the coating film having oil repellency is too thin. On the other hand, when the film thickness of the coating film having oil repellency is too thick, sometimes production efficiency of the cover 100 or the retainer 400 deteriorates and production cost increases. Accordingly, the film thickness of the coating film having oil repellency stacked on the surface may be set to 0.1 to 100 µm, for example. In addition, it is only necessary for the coating film having oil repellency to be stacked at least on the inner face of each of the cover 100 and the retainer 400 on which the perfume cartridge 200 is retained. However, it is also possible for the coating film having oil repellency to be stacked on an all faces of each of the cover 100 and the retainer 400.

A method of stacking the coating film having oil repellency is not specifically limited. It is possible to stack the coating film having oil repellency on a surface of the cover 100 or the retainer 400 by using an appropriate method such as immersion or spray coating.

In addition, in the case where the structure having oil repellency is provided on the inner face of at least one of the cover 100 and the retainer 400, the structure having oil repellency may include a fine structure formed on a surface of the cover 100 or the retainer 400, for example. Such a fine structure may include protrusions or recess parts of 1 µm or less, for example.

Figure 33:
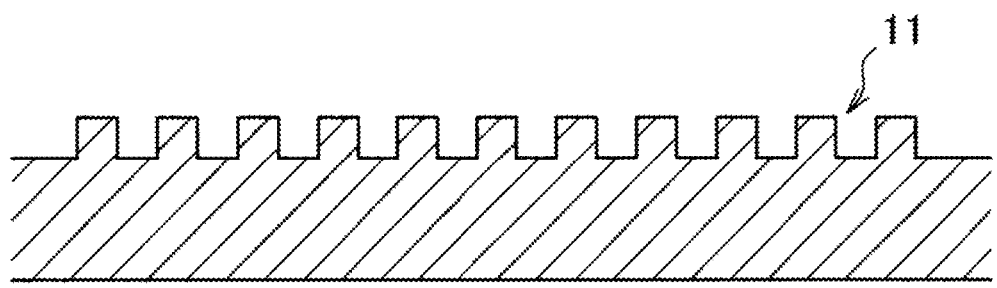
FIG. 33 is an explanatory diagram illustrating an example of a structure with oil repellency.
Figure 34:
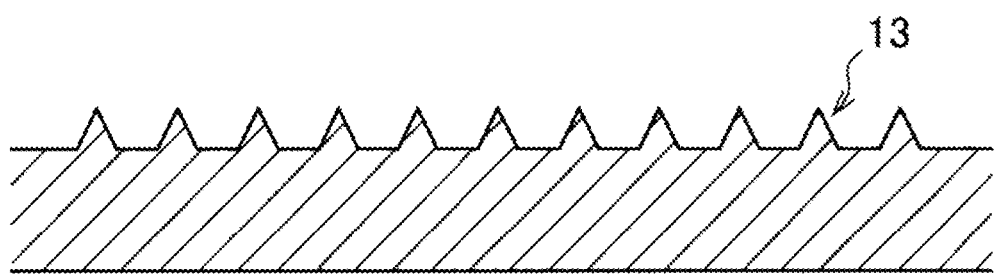
FIG. 34 is an explanatory diagram illustrating another example of a structure with oil repellency.
Figure 35:
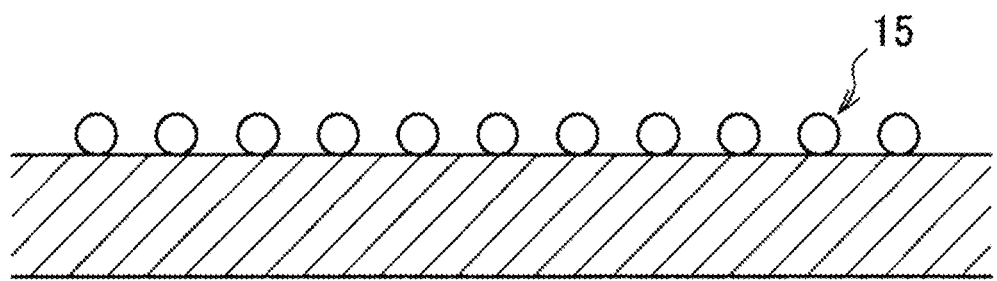
FIG. 35 is an explanatory diagram illustrating another example of a structure with oil repellency.

FIG. 33 to FIG. 35 illustrates examples of the structure having oil repellency. The structure having oil repellency illustrated in FIG. 33 includes repetitive patterns of rectangular protrusions (or recess parts) 11 formed on the surface of the cover 100 or the retainer 400. In addition, the structure having oil repellency illustrated in FIG. 34 includes repetitive patterns of triangular protrusions 13 formed on the surface of the cover 100 or the retainer 400. In addition, the structure having oil repellency illustrated in FIG. 35 includes nanoparticles 15 attached on the surface of the cover 100 or the retainer 400. The structure having oil repellency does not have to include such repetitive patterns with protrusions/recess parts. It is possible to include a portion with protrusions/recess parts of different shape or different density from other portions.

The drug resistance of the cover 100 or the retainer 400 can be improved by including at least one of such a coating film having oil repellency or such a structure having oil repellency. Therefore, it is possible to protect the cover 110 or the retainer 400 from the chemical attack due to the evaporated perfumes or the liquid perfumes leaking from the perfume cartridge 200.

5. Perfume Leakage Prevention Structure

Next, a perfume leakage prevention structure will be described. When a liquid perfume leaks from the perfume cartridge 200 retained in the cover 100 and the retainer 400, the perfume leakage prevention structure prevents additional leakage of the liquid perfume to an outside of the cover 100 and the retainer 400.

Figure 36:
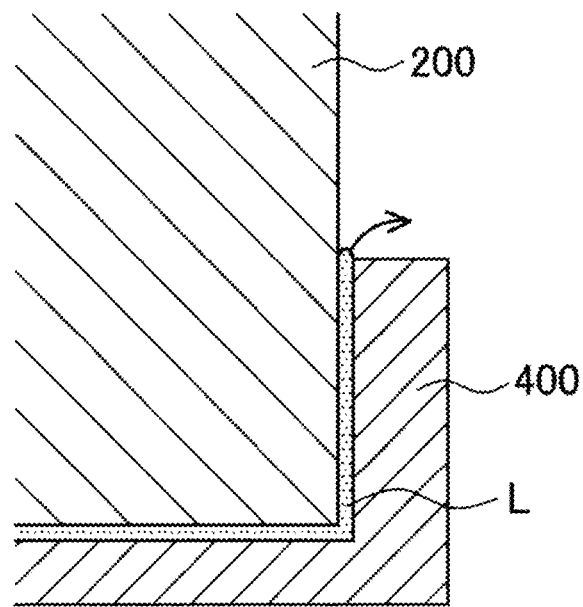
FIG. 36 is an explanatory diagram illustrating leakage of a perfume.

For example, in the case where the perfume cartridge 200 is a reusable perfume cartridge in which the air flow channels 210 are capable of being refilled with liquid perfumes, there is the potential for leakage of a perfume from the other end of the air flow channel 210 when detaching any of the cover 100 and the retainer 400 and injecting the perfume into the air flow channel 210. For example, as illustrated in FIG. 36, in the case where the rear-side end of the perfume cartridge 200 retained by the retainer 400 has a cylindrical shape with an even outer periphery and a liquid perfume is injected into the front-side end of an air flow channel 210 while detaching the cover 10, the liquid perfume L may pass through a gap between the perfume cartridge 200 and the retainer 400 and leak from the air flow channel 210 of the perfume cartridge 200 to an outside.

In the case where the gap between the perfume cartridge 200 and the retainer 400 is narrow, capillary action is considered to cause the liquid perfume L to leak to the outside. When the liquid perfume L further leaks to the outside of the cover 100 and the retainer 400, there is a possibility that the leaked perfume deteriorates surrounding components and the perfume adheres to things around the aroma provision device 1 such as fingers.

Figure 37:
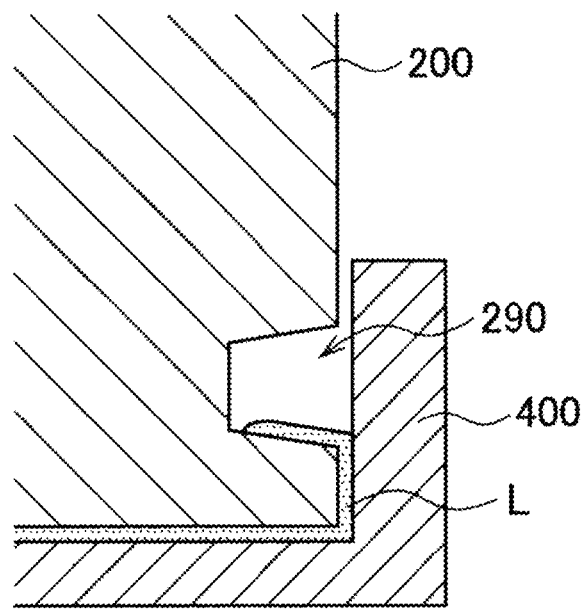
FIG. 37 is an explanatory diagram illustrating an example of a perfume leakage prevention structure.

FIG. 37 is an explanatory diagram illustrating the perfume cartridge 200 with the perfume leakage prevention structure. The perfume leakage prevention structure has a recess part 290 on an outer periphery of a portion of the perfume cartridge 200 arranged in the retainer 400. The recess part 290 extends in the circumferential direction. The recess part 290 provided on the outer periphery of the perfume cartridge 200 is capable of capturing the liquid perfume leaked from the rear-side end of the air flow channel 210 of the perfume cartridge 200 while the liquid perfume is passing through the gap between the perfume cartridge 200 and the retainer 400. This enables to prevent additional leakage of the liquid perfume to the outside of the retainer 400.

Cross-sectional shapes of the recess part 290 serving as the perfume leakage prevention structure are not specifically limited. As illustrated in FIG. 37 a cross-sectional shape of the recess part 290 may be a trapezoidal shape. Alternatively, a cross-sectional shape of the recess part 290 may be a various shape such as a half-circle shape, a half-oval shape, a rectangular shape, or a triangular shape. In addition, the width and the depth of the recess part 290 are not specifically limited. It is only necessary for the recess part 290 to be in a range facing the inner periphery of the retainer 400. In addition, the recess part 290 is preferably formed such that the thickness of the structural part between the recess part 290 and the air flow channels 210 arranged in the perfume cartridge 200 does not get too thin. In addition, it is possible to form a plurality of recess parts along the axial direction of the perfume cartridge 200.

Figure 38:
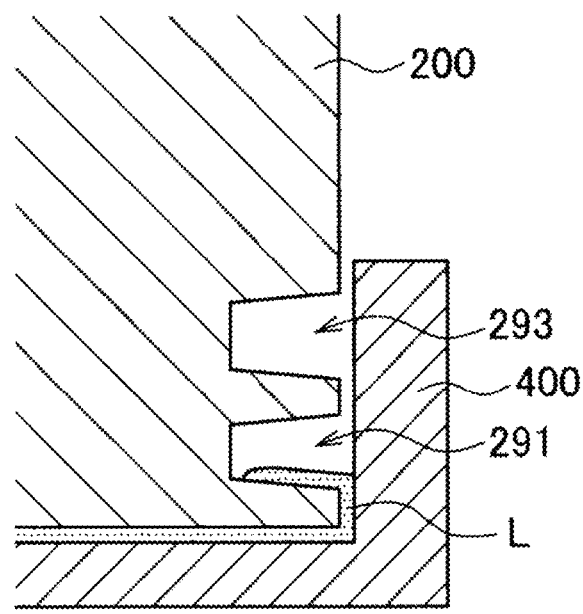
FIG. 38 is an explanatory diagram illustrating another example of a perfume leakage prevention structure.

FIG. 38 is an explanatory diagram illustrating an example of a perfume leakage prevention structure having two recess parts 291 and 293 along the axial direction of the perfume cartridge 200. In this perfume leakage prevention structure, the first recess part 291 captures a liquid perfume passing through the gap between the perfume cartridge 200 and the retainer 400. In addition, if the liquid perfume skips the first recess part 291, the second recess part 923 captures the liquid perfume. Accordingly, such a perfume leakage structure is capable of surely preventing leakage of the liquid perfume to the outside of the retainer 400.

EXAMPLES

Next, examples of the structure for protecting the cover 100 and the retainer 400 in the aroma provision device 1 according to the above-described embodiment will be described. In the following examples, presence or absence of deterioration in the cover 100 or the retainer 400 that retain the perfume cartridge 200 is compared between a case where the coating film having oil repellency is stacked on an inner face of at least one of the cover 100 and the retainer 400 and a case where no coating film having oil repellency is stacked thereon.

In examples 1 to 5, five test specimens (5 mm square and thickness of 1 mm) are immersed for three minutes in a fluorinated coating (DURASURF (DS-5210S135) made by Harves Co., Ltd.), thereby coating the test specimens with a fluorine coating. The test specimens are ABS resins serving as polymeric resin capable of being used as a component of the cover 100 or the retainer 400. In addition, cracks in each of the test specimens are visually observed after an aroma oil (perfume) is delivered into each of the obtained test specimens drop by drop, each of the test specimens is put in an aluminum bag, and then the test specimens are left for 12 hours under the condition of an ambient temperature of 65° and a relative humidity of 80% RH.

In addition, in the examples 6 to 10, five test specimens of ABS resin are also used in a way similar to the examples 1 to 5. However, the test specimens are not subjected to the fluorine coating in the examples 6 to 10. Cracks in each of the test specimens of the examples 6 to 10 are visually observed after the test specimens are left for 12 hours under the same condition. Results thereof are shown in Table 1.

TABLE 1

|  | Crack |
| --- | --- |
| Example 1 | Not exist |
| Example 2 | Not exist |
| Example 3 | Not exist |
| Example 4 | Not exist |
| Example 5 | Not exist |
| Example 6 | Exist |
| Example 7 | Exist |
| Example 8 | Exist |
| Example 9 | Exist |
| Example 10 | Exist |

As shown in Table 1, no crack is observed with respect to the surfaces of the test specimens subjected to the fluorine coating in the examples 1 to 5. On the other hand, cracks are observed with respect to the surfaces of the test specimens that are not subjected to fluorine coating in the examples 6 to 10. These results show that it is possible to protect the cover 100 or the retainer 400 from the chemical attack due to a liquid perfume or an evaporated perfume by subjecting at least an inner face of the cover 100 or the retainer 400 to the fluorine coating.

As described above, each of the air flow channels of the perfume retainer member (perfume cartridge) according to the embodiment of the present disclosure has the retainer space made in the main body, and a first opening and second opening that open the retainer space to an outside of the main body. Perfumes are retained in the air flow channels such that the wet perfumes are attached to the inner faces of the air flow channels. Therefore, it is possible to prevent the aroma provision device 1 from getting larger and improve the aroma sustainability. In addition, air is introduced into or output from the retainer space via the first opening and the second opening. In the retainer space, most of the perfumes are retained in the perfume cartridge according to the embodiment. Since the perfumes are retained in the retainer spaces such that the perfumes are attached to the inner faces of the retainer spaces, there is no possibility of leakage of the liquid perfume, and it is possible to use the first opening and the second opening with relatively large internal diameters.

Therefore, it is possible to increase an amount of air flowing in the air flow channel, and it is possible to efficiently output aroma.

In addition, in the case where the perfume cartridge according to the embodiment includes a surface increase part configured to widen an internal surface of the retainer space, it is possible to further increase an amount of perfumes to be retained in the retainer space. Therefore, it is possible to prevent the aroma provision device 1 from getting larger and improve the aroma sustainability more.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)
A perfume retainer member including:
a retainer space that is made in a main body to retain a perfume; and
a first opening and a second opening configured to open the retainer space to an outside of the main body,
in which an air flow channel includes the retainer space, the first opening, and the second opening.

(2)
The perfume retainer member according to (1),
in which the retainer space includes a segment region having a diameter of 3000 µm or less.

(3)
The perfume retainer member according to (2),
in which the retainer space includes a segment region having a diameter of 1000 µm or less.

(4)
The perfume retainer member according to any one of (1) to (3),
in which the retainer space includes a plurality of segment regions combined with each other, each of the segment regions having a diameter of 3000 µm or less.

(5)
The perfume retainer member according to (4),
in which structures of a plurality of the flow channels include at least one segment region having a diameter of 1000 µm or less.

(6)
The perfume retainer member according to any one of (1) to (5),
in which the retainer space includes a plurality of segment regions having different pressure drops when air flows.

(7)
The perfume retainer member according to (6),
in which the plurality of segment regions having the different pressure drops are arranged in parallel with respect to an air flow.

(8)
The perfume retainer member according to (6) or (7),
in which the plurality of segment regions have the different pressure drops since at least one of the segment regions includes a surface increase part configured to increase a surface area of the air flow channel.

(9)
The perfume retainer member according to (8),
in which the surface increase part includes a structural part having rotational symmetry around a predetermined axis in the segment region, a structural part having translational symmetry in a predetermined axial direction in the segment region, or a structural part having reflection symmetry in a predetermined axial direction in the segment region.

(10)
The perfume retainer member according to (8) or (9),
in which the surface increase part includes a structural part having a cross shape whose intersection is on a predetermined axis in the segment region.

(11)
The perfume retainer member according to any one of (6) to (10),
in which the plurality of segment regions have different cross-sectional areas of flow channels, and therefore have the different pressure drops.

(12)
The perfume retainer member according to any one of (1) to (11),
in which the main body includes an organic polymeric material, and the perfume is retained such that the perfume infiltrates in the main body.

(13)
The perfume retainer member according to any one of (1) to (12), including
a plurality of the air flow channels each of which includes the retainer space, the first opening, and the second opening,
in which at least a plurality of the first openings or a plurality of the second openings are arranged at regular intervals around a predetermined central axis of the perfume retainer member.

(14)
The perfume retainer member according to (13),
in which at least the plurality of first openings or the plurality of second openings are arranged on both end faces in an axial direction of the predetermined central axis of the perfume retainer member.

(15)
The perfume retainer member according to any one of (1) to (14), including
a seal member configured to seal the first opening or the second opening.

(16)
An aroma provision device including:
a perfume retainer member including an air flow channel that includes
  a retainer space that is made in a main body to retain a perfume, and
  a first opening and a second opening configured to open the retainer space to an outside of the main body; and
an air blow source configured to supply air to the air flow channel.

REFERENCE SIGNS LIST 1 aroma provision device
200 perfume retainer member (perfume cartridge)
202 main body
210 air flow channel
213 first opening
214 second opening 250 retainer space
251 first segment region
253 second segment region
255 third segment region

The invention claimed is:

1. A perfume retainer member comprising:
  a main body; and
  a plurality of air flow channels located in the main body, each of the plurality of air flow channels including:
    a retainer space configured to retain a perfume,
    a first opening located at a first end of the air flow channel and connecting a first end of the retainer space to a space outside of the first end of the air flow channel, and
    a second opening located at a second end of the air flow channel and connecting a second end of the retainer space to a space outside of the second end of the air flow channel,
    wherein the retainer space includes a plurality of segment regions arranged adjacent each other such that an external wall of one of the plurality of segment regions is in contact with an external wall of another of the plurality of segment regions, and
    wherein the plurality of segment regions increase a surface area of the air flow channel without increasing a volume of space of the air flow channel.

2. The perfume retainer member according to claim 1, wherein, for each of the plurality of air flow channels, each of the plurality of segment regions has a diameter of 3000 µm or less.

3. The perfume retainer member according to claim 1, wherein, for each of the plurality of air flow channels, each of the plurality of segment regions has a diameter of 1000 µm or less.

4. The perfume retainer member according to claim 1, wherein, for each of the plurality of air flow channels, at least one of the plurality of segment regions has a diameter of 3000 µm or less.

5. The perfume retainer member according to claim 1, wherein, for each of the plurality of the flow channels, at least one of the plurality of segment regions a diameter of 1000 µm or less.

6. The perfume retainer member according to claim 1, wherein, for each of the plurality of air flow channels, the plurality of segment regions have different pressure drops when air flows in the air flow channel.

7. The perfume retainer member according to claim 6, wherein, for each of the plurality of air flow channels, the plurality of segment regions are arranged in parallel with respect to an air flow in the air flow channel.

8. The perfume retainer member according to claim 7, wherein, for each of the plurality of air flow channels, the plurality of segment regions have the different pressure drops due to a surface-increase structure in at least one of the plurality of segment regions, the surface-increase structure being configured to increase the surface area of the air flow channel.

9. The perfume retainer member according to claim 8, wherein the surface-increase structure includes:
  a structural part having rotational symmetry around a predetermined axis of a corresponding segment region, or
  a structural part having translational symmetry in an axial direction of the predetermined axis of the corresponding segment region, or
  a structural part having reflection symmetry in the axial direction of the predetermined axis of the corresponding segment region.

10. The perfume retainer member according to claim 8, wherein the surface-increase structure includes a structural part having a cross shape whose intersection is on a predetermined axis of a corresponding segment region.

11. The perfume retainer member according to claim 6, wherein the plurality of segment regions have different cross-sectional flow areas, and therefore have the different pressure drops.

12. The perfume retainer member according to claim 1, wherein the main body includes an organic polymeric material, and the perfume is retained such that the perfume infiltrates in the main body.

13. The perfume retainer member according to claim 1, wherein at least some of the first openings or at least some of the second openings or at least some of the first and second openings of the plurality of air flow channels are arranged at regular intervals around a predetermined central axis of the perfume retainer member.

14. The perfume retainer member according to claim 13, further comprising end faces located at opposite ends of the main body, wherein the at least some of first openings or the at least some of second openings or the at least some of the first and second openings of the plurality of air flow channels are arranged on both of the end faces in an axial direction of the predetermined central axis of the perfume retainer member.

15. The perfume retainer member according to claim 1, further comprising a seal member configured to seal the first opening or the second opening of each of the plurality of axial flow channels.

16. An aroma provision device comprising:
  a perfume retainer member including:
    a main body,
    a plurality of air flow channels located in the main body, each of the plurality of air flow channels including:
      a retainer space configured to retain a perfume, and
      a first opening located at a first end of the air flow channel and connecting a first end of the retainer space to a space outside of the first end of the air flow channel, and
      a second opening located at a second end of the air flow channel and connecting a second end of the retainer space to a space outside of the second end of the air flow channel,
      wherein the retainer space includes a plurality of segment regions arranged adjacent each other such that an external wall of one of the plurality of segment regions is in contact with an external wall of another of the plurality of segment regions, and
      wherein the plurality of segment regions increase a surface area of the air flow channel without increasing a volume of space of the air flow channel; and
  an air blower configured to supply air to the plurality of air flow channels.

* * * * *